(12) United States Patent
Turi et al.

(10) Patent No.: US 6,413,249 B1
(45) Date of Patent: Jul. 2, 2002

(54) DISPOSABLE ABSORBENT ARTICLE HAVING ELASTICALLY CONTRACTIBLE WAIST AND SIDES

(75) Inventors: Mordechai Turi, Mill Hall, PA (US); Michael Kauschke, Yonkers, NY (US)

(73) Assignee: First Quality Enterprises, Inc., McElhattan, PA (US)

( * ) Notice: Subject to any disclaimer, the term of this patent is extended or adjusted under 35 U.S.C. 154(b) by 0 days.

(21) Appl. No.: 09/097,198

(22) Filed: Jun. 12, 1998

(51) Int. Cl.[7] .............................................. A61F 13/15
(52) U.S. Cl. .................... 604/387; 604/385.1; 604/392; 604/386
(58) Field of Search .............................. 604/387, 385.1, 604/392, 386, 391

(56) References Cited

U.S. PATENT DOCUMENTS

H1440 H  *  5/1995  New et al. .................. 604/386
5,722,968 A  *  3/1998  Datta et al. .................. 604/391

* cited by examiner

Primary Examiner—John G. Weiss
Assistant Examiner—Michele Kidwell

(57) ABSTRACT

An integral disposable elasticized absorbent article is provided for use as infant training pants or adult incontinent underpants, briefs and the like. The article comprises an absorbent body having a liquid pervious top layer, a liquid impervious backsheet and a liquid absorbent layer therebetween. A pair of elasticized members (belts) are secured to the absorbent body, with one elasticized member being disposed substantially parallel to the left of the longitudinal axis of the article, and the second elasticized member being disposed substantially parallel to the right of the longitudinal axis of the article. Each elasticized member has an end closure means adapted to engage the end closure means of the other elastic member to secure the absorbent article firmly to the body of the wearer.

12 Claims, 30 Drawing Sheets

DISPOSABLE ABSORBENT ARTICLE HAVING ELASTICALLY CONTRACTIBLE WAIST AND SIDES

FIELD OF THE INVENTION

The present invention relates generally to absorbent article such as disposable diapers, and is more particularly related to infant training pants and adult incontinent underpants, briefs and guards used for absorption and containment of urine and other body exudates. In one particular aspect, the present invention relates to such adult incontinent articles which are easy to wear, securely fit against the body contours for effective prevention against leakage of urine and other body exudates, and which are also easy to remove.

BACKGROUND OF THE INVENTION

Disposable absorbent articles such as disposable baby diapers and adult incontinent briefs, underpants, guards and the like articles are widely used in homes and various health care facilities and institutions. Indeed the use of such articles have become a common sanitary practice, and while initially such absorbent articles were used mostly for baby care, more recently their use has expanded for adults as well. In both instances, the absorbent article must be designed to effectively prevent leakage of urine and other fecal materials, while insuring body fit and comfort.

Present commercially available absorbent articles are generally unitary in structure, pre-shaped and pre-folded, and comprise an absorptive pad having a liquid permeable top sheet facing the wearer's body, a liquid impermeable backsheet on the opposite side, and an absorbent sheet or panel disposed between the top sheet and the back sheet. The absorbent article comprises a front side portion, a crotch portion and a backside portion, and further includes elastic members along the circumference of the waist and around the leg openings. While the heretofore commercially available absorbent articles have been somewhat effective against leakage of body fluids and fecal materials, and have therefore met some degree of acceptability, they have not been entirely satisfactory for their intended applications. In other words, they have not proven to be entirely leak proof, nor have they completely prevented issuance of the body exudates outside the diaper or the underpants. These deficiencies are primarily due to inadequate and loose body fit, which result in leakage of the body fluids and solids through the legs' openings. These problems are even more pronounced in case of adults because of their diverse body shapes and varying contours. Another disadvantage of the commercially available absorbent articles such as diapers, incontinent briefs and the like, is associated with the ability of opening and removing the soiled article without soiling the wearer's legs or body.

There is a plethora of patents which disclose the different attempts made by the prior art workers over the years to eliminate, or at least minimize, the shortcomings of the present commercially available absorbent articles.

For example, U.S. Pat. No. 4,909,804 issued to Herman Douglas, Jr. on Mar. 20, 1990 discloses a child toilet training pant which has a means for elasticizing the leg and waist openings by elastic bands at the waist and leg openings. The training pant described in that patent is provided with a separable side seem from the waistband to the legband on both sides in order to permit easy removal of the toddler's pant when soiled. This article does not provide for examination of the condition of the diaper and requires tearing the side seams to remove the diaper which can thus result in soiling the toddler as well as the applier.

U.S. Pat. No. 5,569,234 issued to Kenneth B. Buell et al. on Oct. 29, 1996 describes a pull-on garment provided with a continuous belt in the front region and the back region to distribute the forces generated during use in order to better fit the pull-on garment on the wearer. As in the above-mentioned patent to Douglas, Jr., the article described in Buell et al. does not provide for examination of the condition of the diaper and requires tearing a side seam for its removal, thus also causing soiling to the wearer and applier of the garment.

U.S. Pat. No. 5,607,416 issued to Masamitsu Yamamoto et al. on Mar. 4, 1997 describes a disposable absorbent pad comprising a pad member adapted to be formed into a boat shape under the contractible forces of elastic members contained in side flaps, and an elastic support member; longitudinally opposite sides of the pad member being connected to the front and rear sides of the support member by end flaps. Each of the end flaps comprises a top sheet and a back sheet and is divided in a pair of end flap halves by a slit so as to function as a suspending strap. The end flaps halves are set apart in a V-shape with the slit therebetween as the support members is stretched and contributes to suspend the pad member with high stability. The absorbent pad described in the Yamamoto et al. patent does not provide for forces to counteract the weight of the soiled pad which eventually stretches the crotch region and thus may cause leakage of urine and other body exudates through the leg openings.

U.S. Pat. No. 5,204,997 issued to Migaku Suzuki et al. on Apr. 27, 1993 describes a disposable pant-type garment, such as a diaper of the pant type, which is constructed by attaching elastic surrounding flaps around the leg openings and the waist opening. This garment however is not elastically integral between the crotch and the waist portions and is not adjustable around the waist to conformably fit the body shape. Nor does this garment allow adjustment or refastening of the elastic flaps to insure body fit when the garment is soiled.

The foregoing patents by no means constitute an exhaustive list of the patents which reflect the efforts of the prior art workers in this field, but are merely illustrative for background purposes. As it can be appreciated, however, notwithstanding attempts by others to provide satisfactory absorbent articles for infants as well as for incontinent adults, there is still a need for providing such articles commercially, which are highly effective in preventing leakage of urine and other body exudates, and which are comfortable to wear and conformably fit the body contours so as to insure against such leakage and prevent soiling the wearer's body as well as the person who applies the garment to the wearer.

Accordingly, it is an object of the present invention to provide a disposable absorbent article such as baby diapers, adult incontinent underpants, briefs, guards and the like articles which overcome the deficiencies and shortcomings of the prior art absorbent articles, including the presently commercially available products used for this purpose.

It is another object of this invention to provide such disposable absorbent articles which are provided with a unitary elastically contractible waist and crotch region.

It is also an object of this invention to provide such disposable absorbent articles which have integral refastenable and longitudinally tensionable elastic belts around the waist in order to insure body fit and conformal movements in response to the body shape and contours.

It is yet another object of the present invention to provide disposable absorbent articles having angularity disposed elastic bands (belts) in order to assure drawing of the crotch region laterally and longitudinally toward the waist and hip of the wearer thus providing a more perfect snug fit.

It is still another object of this invention to provide such a disposable absorbent articles which, due to their unique construction, provide improved fit to the body and prevent leakage of urine and other body exudates through the leg openings by drawing the crotch portion towards the hip line of the wearer thus countering the movements of the wearer and the weight of the downstretching of the crotch portion, while maintaining its closeness to the body when the absorbent core is soiled and contains body liquids and other exudates.

The foregoing and other objects and features of the present invention will be more fully comprehended and appreciated from the ensuing detailed description and the various figures in the drawing which form parts of the application.

SUMMARY OF THE INVENTION

The present invention provides uniquely designed and constructed absorbent articles for use as infant diapers and adult incontinent underpants, briefs, guards and the like which overcome the deficiencies and problem associated with the prior art products of this kind. The absorbent article in accordance with the present invention is an integral disposable elasticized article having an absorbent body comprising a liquid pervious top layer facing the body of the wearer, a liquid impervious backsheet, a liquid absorbent layer therebetween, a crotch region and leg openings. The article is provided with elasticized members (belts) which, in one embodiment, are secured to the outside of the article, with one elasticized member being disposed substantially parallel to the left of the longitudinal axis of the article, and other elasticized member being disposed substantially parallel to the right of the longitudinal axis of the article. Each elasticized member has an end portion which is folded laterally outward along the waist at an angle relative to the horizontal axis of the article. In addition, each elasticized member terminates in a closure means which is adapted to inter-engage with a closure means at the end of the other elastic member, thereby securing the absorbent article firmly to the body of the wearer.

Different embodiments of the invention are contemplated wherein the elastic belts are secured to the inside rather than the outside of the absorbent body, and the elastic belts may be substantially parallel to the longitudinal axis of the article or may cross each other at the crotch region in a generally V-shaped configuration. The details of those and other embodiments are described in the ensuring detailed description.

BRIEF DESCRIPTION OF THE DRAWINGS

In the drawings, wherein like reference numerals refer to like parts.

DETAILED DESCRIPTION OF THE INVENTION

Figure 1:
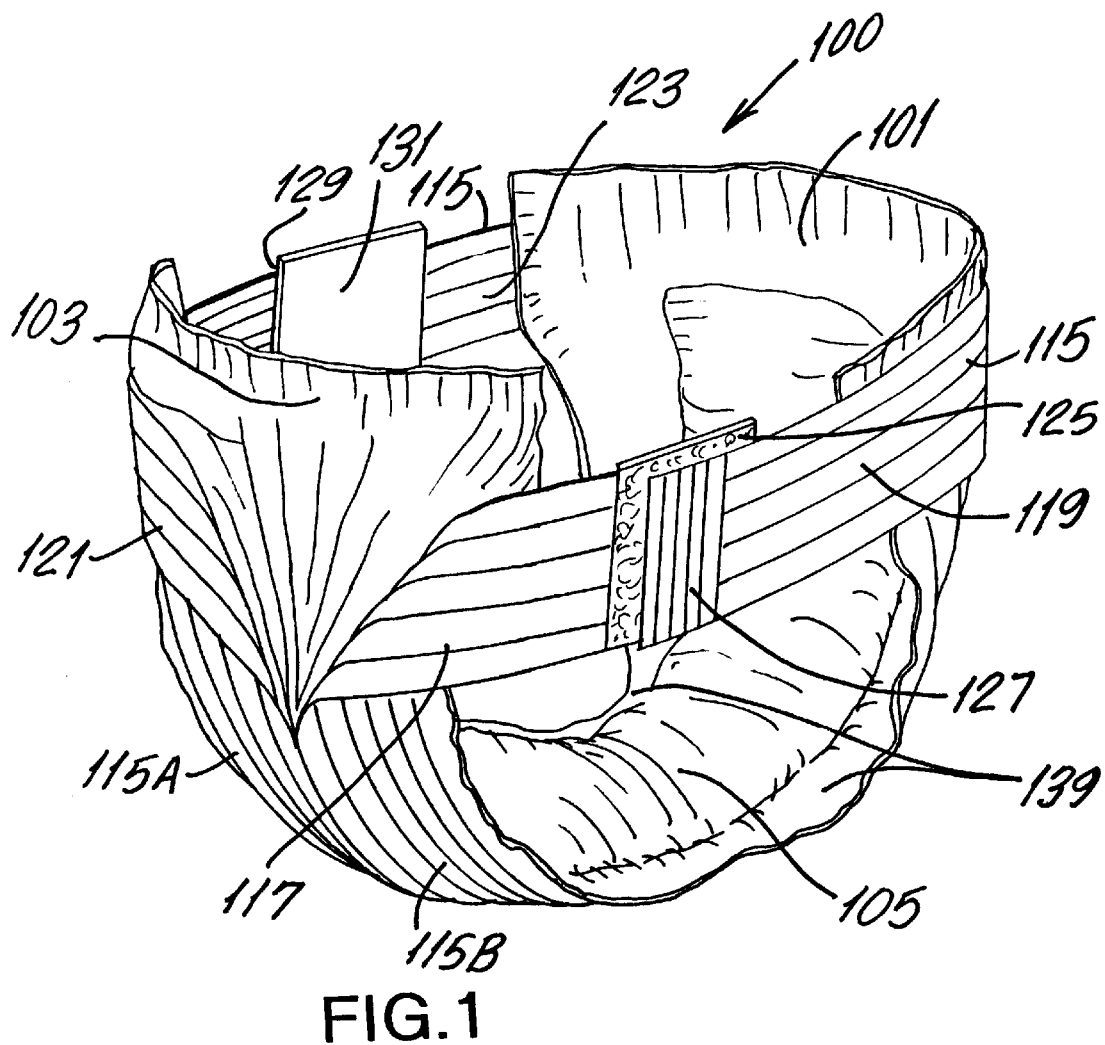
FIG. 1 is a perspective view of an absorbent article made in accordance with one embodiment of the present invention having elastically contractible bands (belts) attached to the outer side of the backsheet of the article, and a closure means at the end of the bands.

Referring to the drawings, and first to FIGS. 1–5, there is shown, in FIG. 1 the absorbent article in the form of a brief, generally designated as 100. The term "brief" as used herein is intended to refer to disposable garments worn below the lower part of the torso by incontinent person, and also encompasses other disposable articles such as baby diapers, adult incontinent underpants, guards, and the like articles. The absorbent article 100 comprises a back waist portion 101, a front waist portion 103 and a crotch region 105. The crotch portion 105 comprises a liquid pervious top sheet or layer 107 facing the body of the wearer, a liquid impervious backsheet or layer 19 which is usually coextensive with the top sheet 107 (see FIG. 5) and an absorbent layer or pad 111 disposed between the backsheet 109 and the top sheet 107. An acquisition layer 113 is disposed between the backsheet layer 109 and the liquid pervious layer 107 and serves to temporarily retain the body exudate and slowly distribute them through the absorbent layer 111. These layers are sealed together at their ends to form a composite sheet.

In the embodiment of the invention illustrated in FIGS. 1–5, the absorbent article 100 is provided with the elastic or belts 115 which are disposed outside the circumference of the absorbent article and are secured to each other at the ends of the belts as hereinafter described. The elastic belt 115 to the left of the longitudinal axis of the article comprises a left longitudinal portion 115A disposed generally parallel to the longitudinal axis of the article, and is folded laterally outward into a left hand front band portion 117 and a left hand rear band portion 119 (see FIG. 2). The elastic belt 115 to the right of the longitudinal axis comprises a longitudinal portion 115B also disposed generally parallel to the longitudinal axis of the article and which is also folded laterally outward into a right hand front band portion 121 and a right rear band portion 123. Each of the band portions terminate in a closure tab adapted to secure the belts together. Thus, the left hand front band portion 117 terminates in the closure tab 125 and the left hand front belt portion 119 terminates in the closure tab 127. Similarly, the right hand front band portion 121 terminates in the closure tab 129 and the right hand rear belt portion 123 terminates in the closure tab 131. The closure tabs 125, 127, 129 and 131 may be covered by areas of Velcro® material as shown in FIG. 1, which can overlap each other to securely engage the respective ends of the belts when the belts are tensioned to adjust to the waist of the wearer. It can be appreciated, however, that the end closure tabs may be areas provided with clips or other fastening means for adjustably engaging the closure tabs when the belts are tensioned to adjust to the body waist.

In order to assure a more perfect fit of the absorbent article to the body of the wearer, each of the band portions 117, 119, 121 and 123 is folded laterally outward at an angle, preferably at an angle of from about 5 degrees to about 45 degrees relative to the horizontal axis of the absorbent article. Such angular disposition of the band portions permits drawing of the crotch region longitudinally and laterally toward the waist and hip of the wearer and thus assures a more perfect snug fit.

Figure 2:
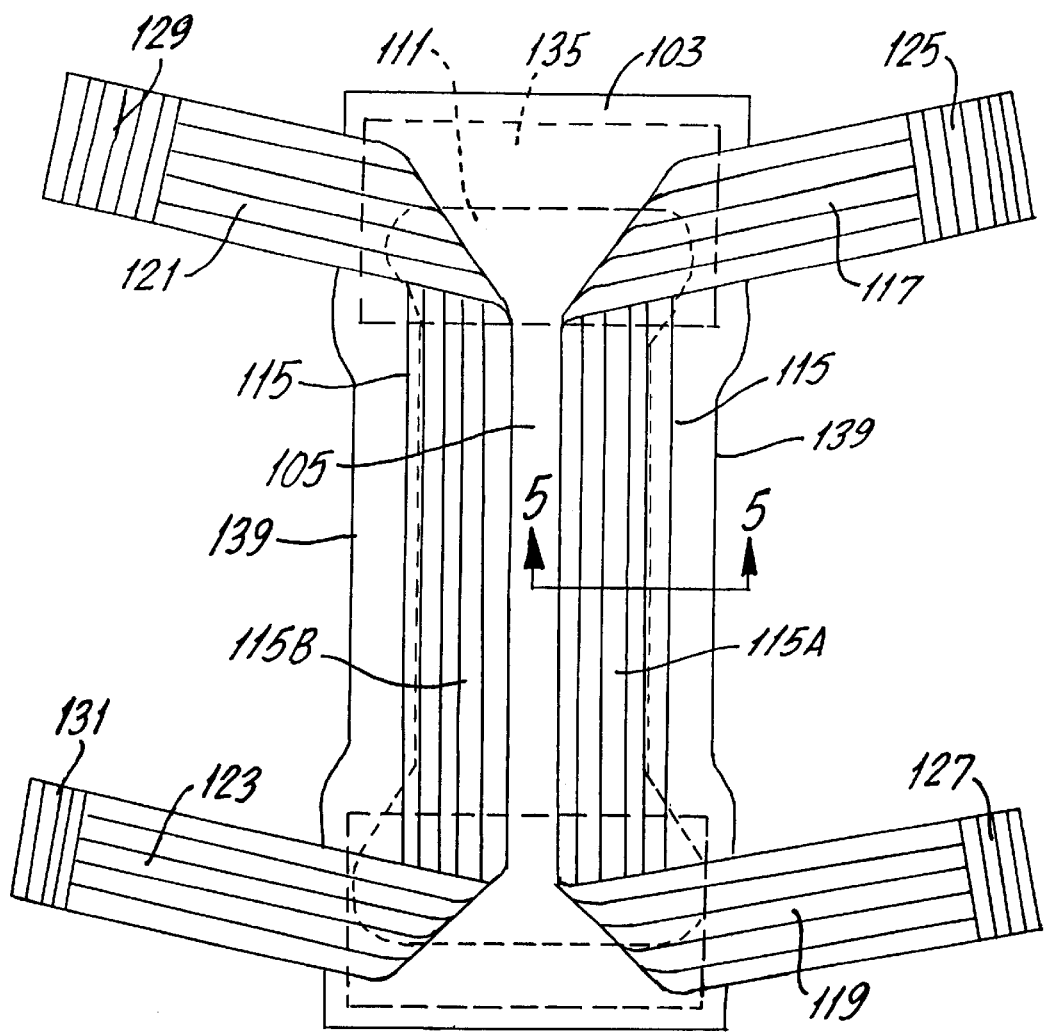
FIG. 2 is a plan view of the absorbent article shown in FIG. 1, in stretched position.

As shown in FIG. 2, the absorbent article 100 is also provided with a back waist reinforcement portion 133 and a front waist reinforcement portion 135 for attachment of the belts as hereinafter described.

The elastic belts 115 are attached to the absorbent article 100 by attaching them to the outer side of the liquid impervious layer 109 by means of a suitable adhesive, such as construction adhesive (non-pressure sensitive) 137. The adhesive is applied as a hot melt, intermittently between the liquid impervious layer 109 and the belts 115 when the elastic elements are in stretched or tensioned position. Thus, the hot melt adhesive may be applied to the elastic belts 115 along its entire length or at equally spaced intervals while the elastic belt is stretched to at least 200 percent of its original length, preferably to from about 200 to about 350 percent of its original length. When the elastic band 115 is allowed to contract, the absorbent article is rendered elastic in the longitudinal directions between the front and back portions of the article and around the circumference of the waist.

If the adhesive is applied at unequal spaced intervals, the elastic band contracts in unequal increments along its length.

The absorbent article 100 also has a pair of leg openings 139. By positioning the elastic bands 115 close to the leg openings, an elastic gasketing seal is formed around each of the leg openings in order to further insure against leakage of the urine and the body exudates.

Figure 4:
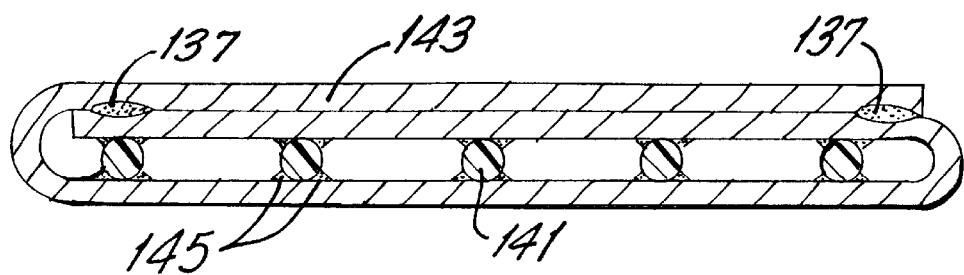
FIG. 4 is a cross sectional view taken along the line 4—4 of FIG. 3.
Figure 3:
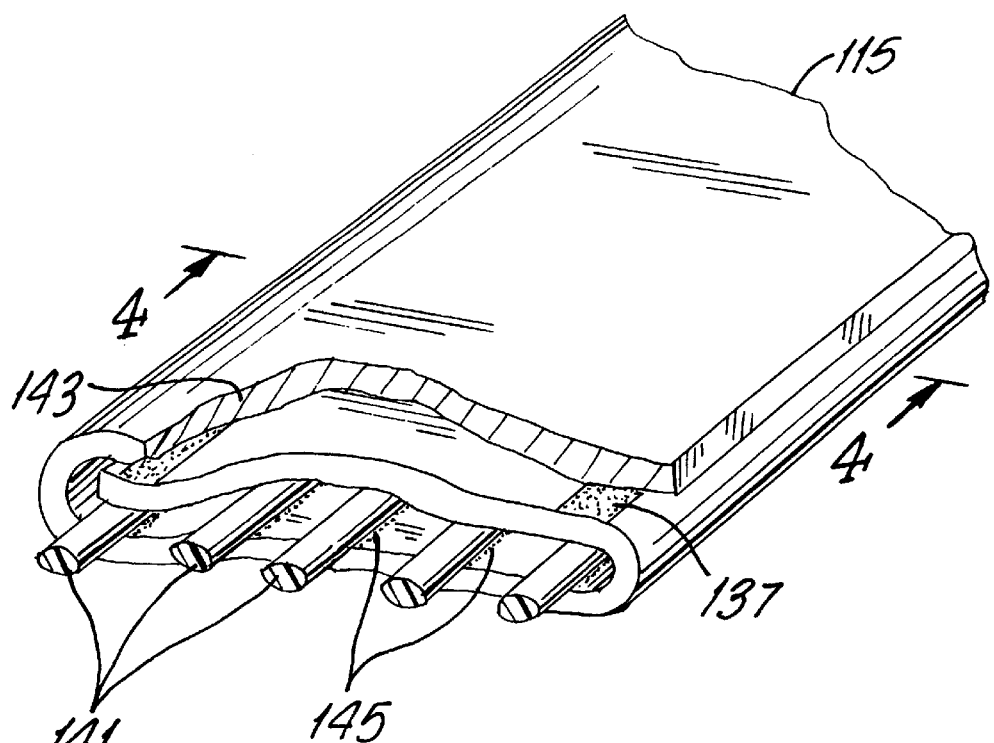
FIG. 3 is a perspective view of the elastically contractible bands in stretched position.
Figure 5:
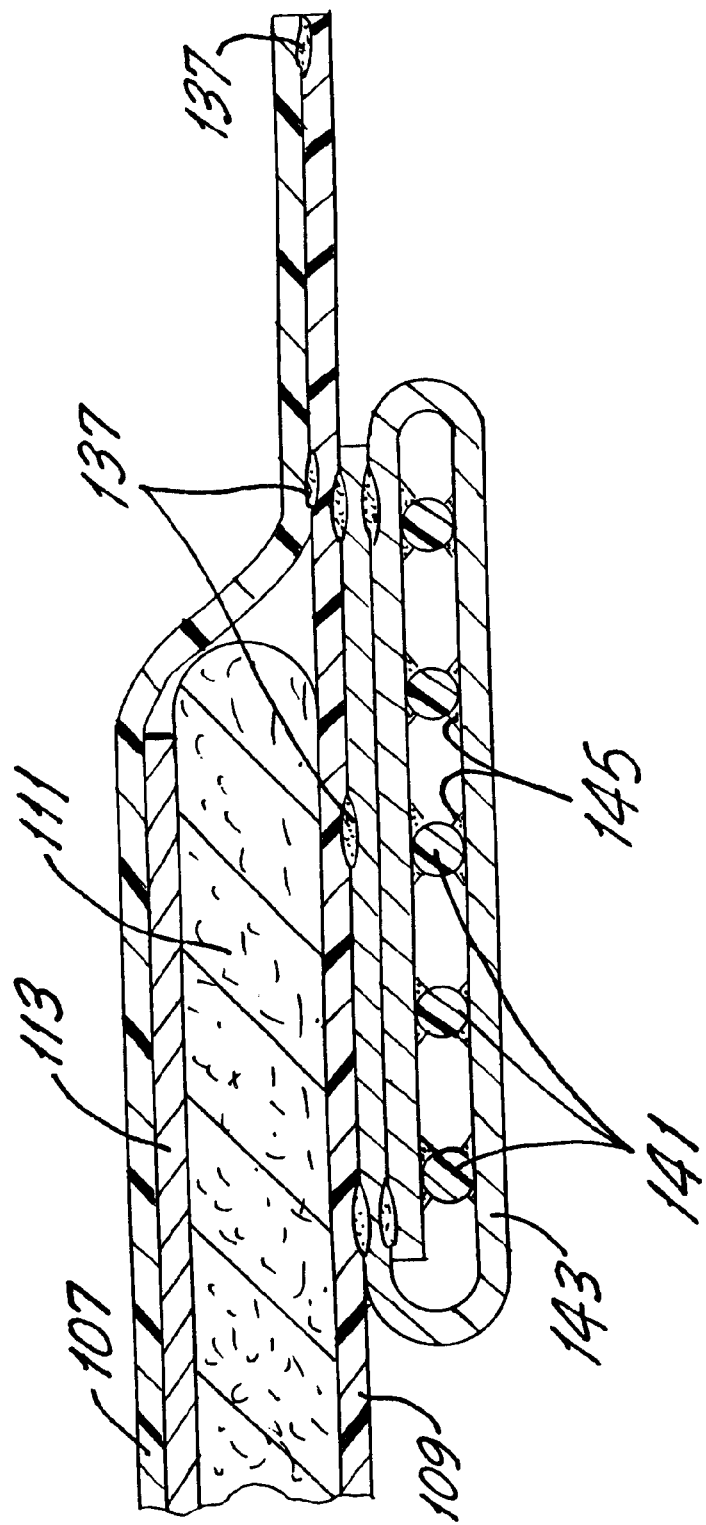
FIG. 5 is a cross sectional view taken along the line 5—5 of FIG. 2 showing the attachment of the bands to the backsheet, and the relative positions of the bands and other components.

Referring to FIGS. 3 and 4, the tensionable elastic belt 115 comprises elastic elements 141 which may be films, foam, elastic strings or strips and spaced in equal or unequal distance relative to each other. The elastic elements 141 are attached to the band wrapping material 143 by means of elastic adhesive 145. The wrapping material 143 envelopes the elastic elements 141 and is secured against unfolding by the construction adhesive 137. The wrapping material 143 may be made of nonwoven fabric, film or a composite thereof. Alternative, the elastic belts 115 may be made of woven or knit elastic fabric.

Figure 2A:
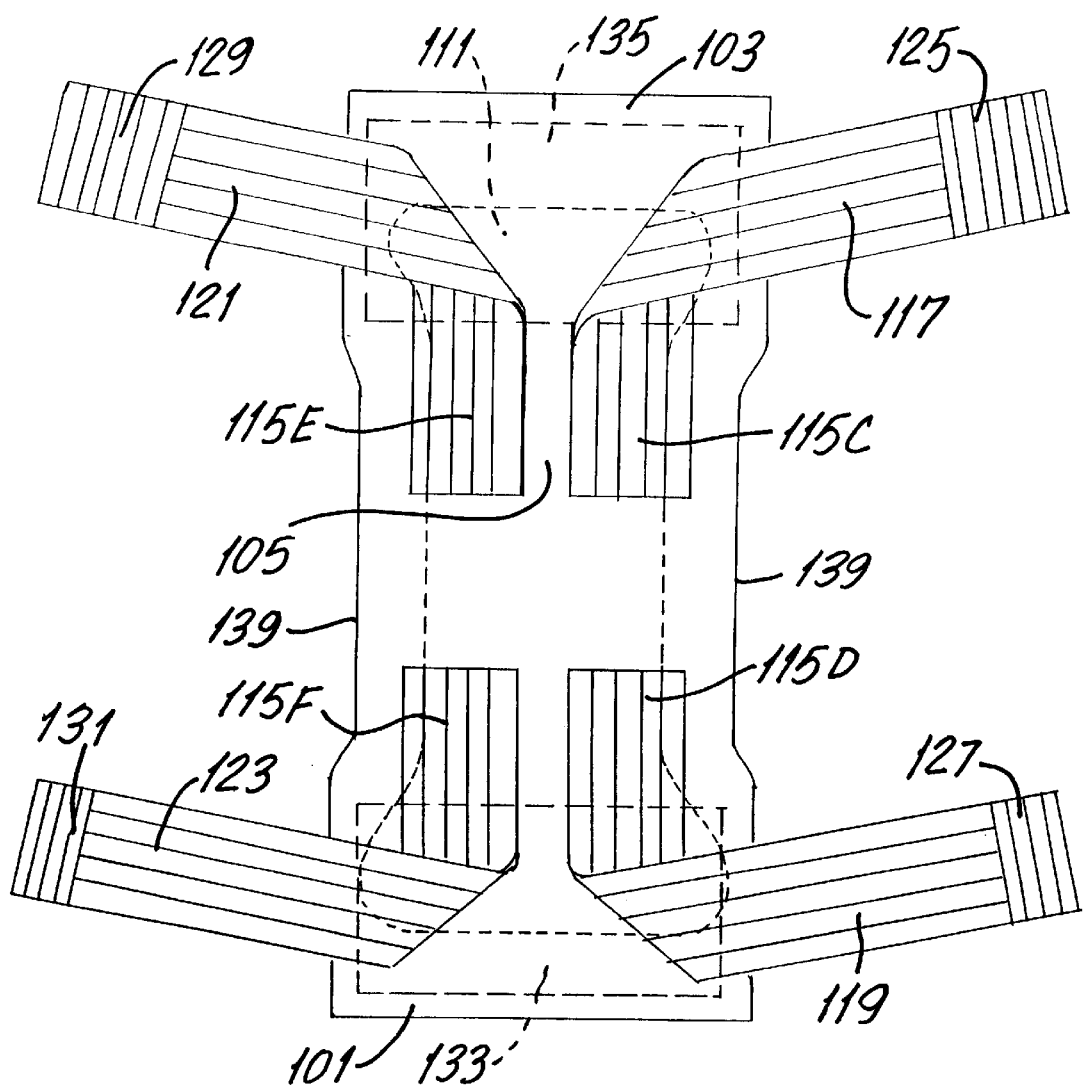
FIG. 2A is view similar to FIG. 2 but, wherein the elastically contractible bands are discontinuous at the mid crotch region.

While in FIG. 2, the longitudinal portions 115A and 115B of the respective elastic bands 115 on the left and right of the longitudinal axis of the absorbent article are shown as continuous bands. In the variation shown in FIG. 2A, these band portions are shown to be discontinuous as in 115C, 115D, 115E and 115F, with each discontinuous band portion having an end terminating at about the mid-crotch region and adhesively secured to the crotch region 105 in spaced apart relationship as shown in FIG. 2A. Otherwise, the construction of the absorbent article is the same as the article shown in FIGS. 1 and 2.

In the preferred practice of the present invention, the elastic belts 115 and the elastic elements 141 are available as System 7000 from the Fulflex Company, Middletown, R.I. and the hot melt adhesive is available from H.B. Fuller Company, St. Paul, Minn. as Code No. HL-1434-X-ZP. The wrapping material 143 may be a 17 gsm polypropylene spunbound polymer available as grade 171LWH from First Quality Fabrics, McElhattan, Pa.

The materials and fabrics used in the construction of the absorbent article of the invention are of the type and variety known in the art and are described in several patents such as, for example, U.S. Pat. No. 4,695,278 and U.S. Pat. No. 4,795,454.

Thus, the liquid pervious top layer 107 is a compliant soft material which is not irritating to the skin. Such material can be made from porous foams, reticulated foams, plastics, natural fibers, such as wood or cotton fibers, synthetic fibers such as polyester or polypropylene fibers, or made from a combination of said materials. A suitable polypropylene material is available from First Quality Fibers, Inc., McElhattan, Pa., as grade 15 ILWH.

The liquid impervious backsheet or layer 109 is preferably manufactured from a thin flexible plastic film such as polyethylene film available from Clopay Plastic Products Company, Cincinnati, Ohio, as grade DH-203.

The absorbent layer 111 may be manufactured from a wide variety of liquid absorbent materials of the type usually used in manufacturing disposable diapers and other absorbent articles. Such materials include comminuted wood pulp, creped cellulose wadding, absorbent foams, absorbent sponges, super absorbent polymers or a combination of said materials.

The acquisition layer 113 is made from a nonwoven material which temporarily retain the exudates and distributes them in the absorbent layer. Such material is available from American Nonwoven Corporation, Columbus, Miss., as grade RB-265-14-B/R.

The construction adhesives employed in the present invention is a hot melt adhesive available from Reynolds Inc., Greensville, S.C. as Reynolds Code No. 51-942.

In use, the disposable absorbent article of the present invention is placed around the waist with the belts tensioned so as to fit snugly but comfortably to the shape of the wearer's body, while the legs extend through the leg openings. The tensioned belts are then secured by securing the respective end closure tabs to one another.

Referring to the embodiment of the invention illustrated in FIGS. 6–9, inclusive, the disposable absorbent article 200 shown therein is provided with the elastic bands (belts) 201 having portions 203 and 205 disposed generally parallel to the longitudinal axis of the article on the left and right sides of said axis. By positioning the elastic bands 201 near the leg openings 207, an elastic sealing gasket is formed along the leg openings 207.

Figure 7:
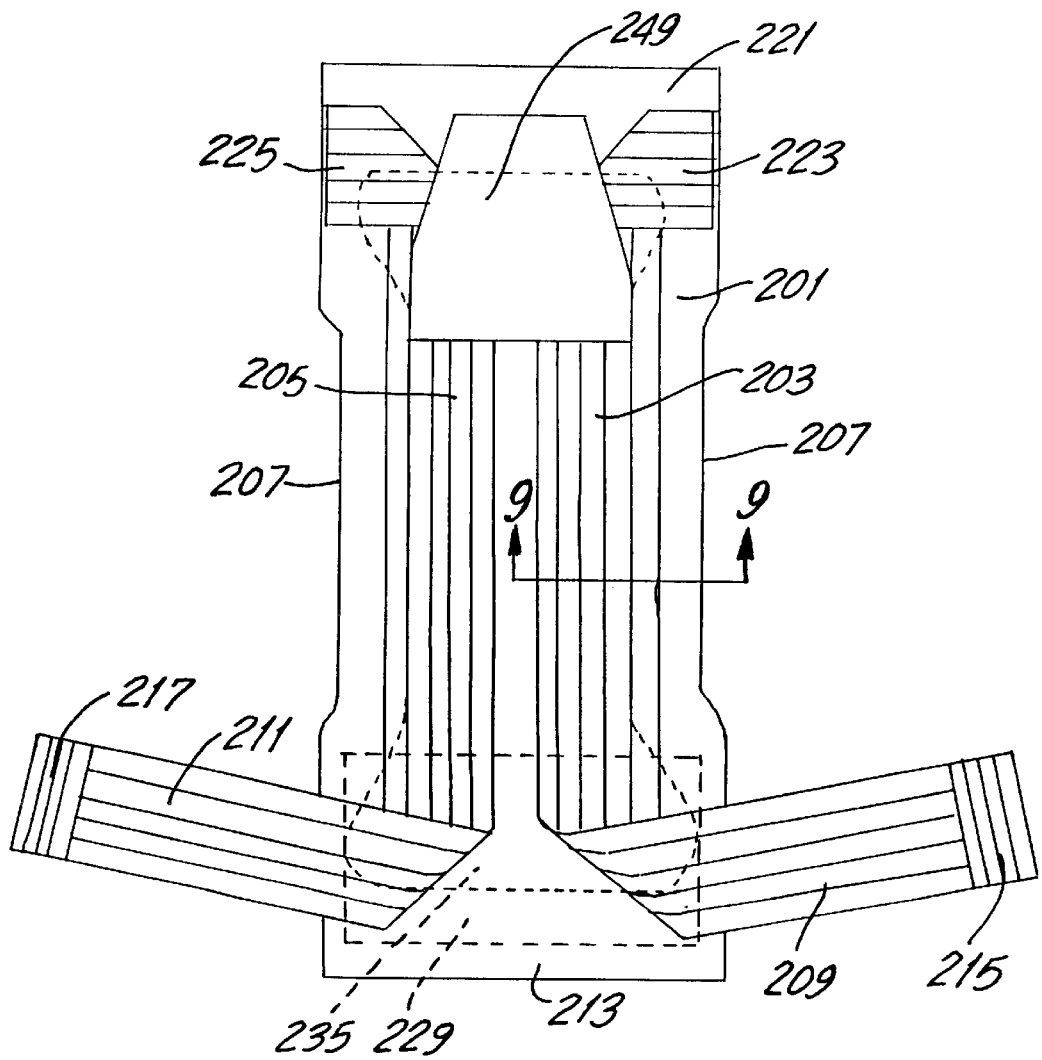
FIG. 7 is a plan view of the embodiment shown in FIG. 6, in stretched position, wherein the front side ends of the bands are folded in the direction of the waist.
Figure 8:
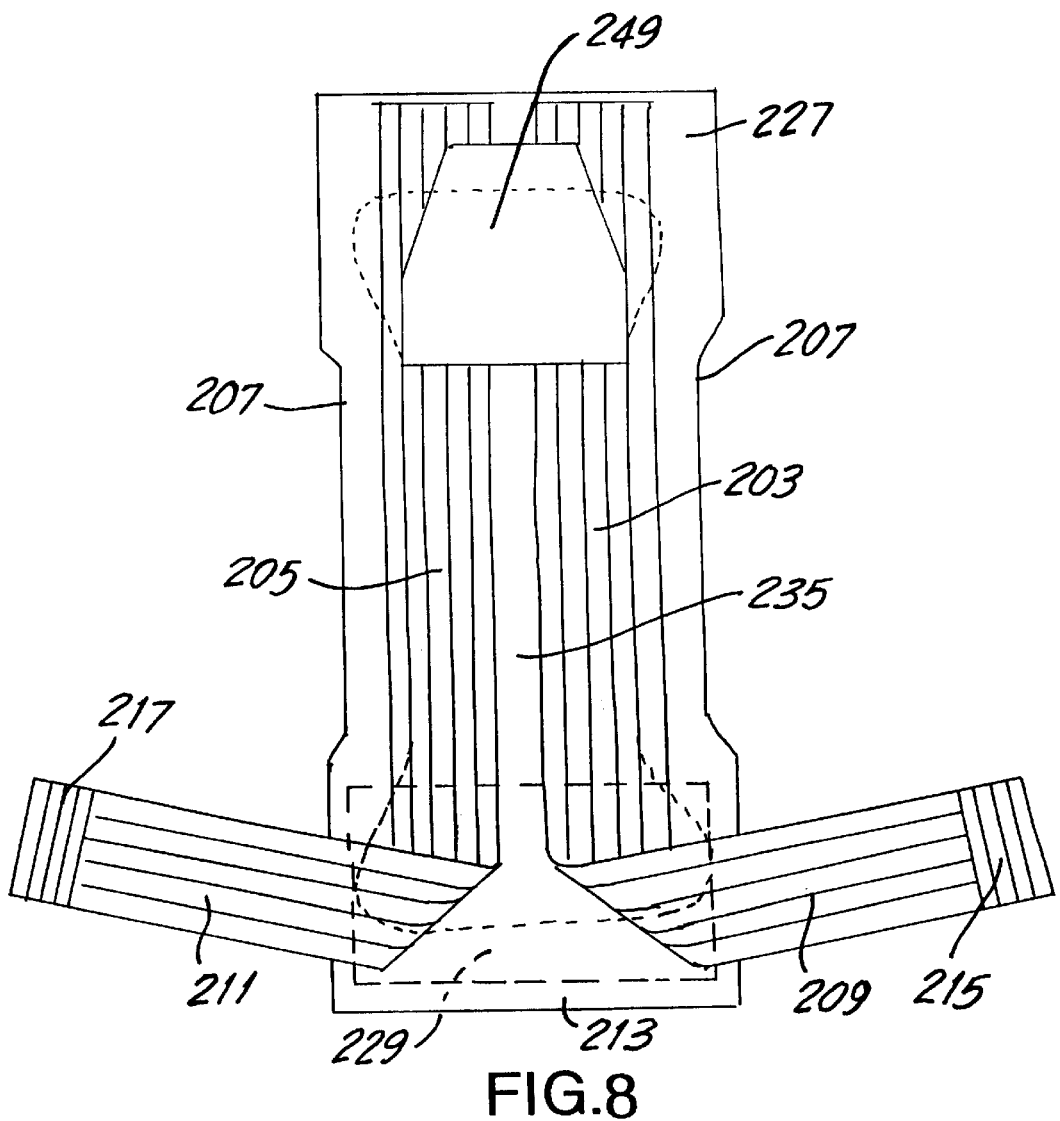
FIG. 8 is a plan view of the embodiment shown in FIG. 6, in stretched position similar to FIG. 7, but wherein the front ends of the bands terminate at the waist.
Figure 9:
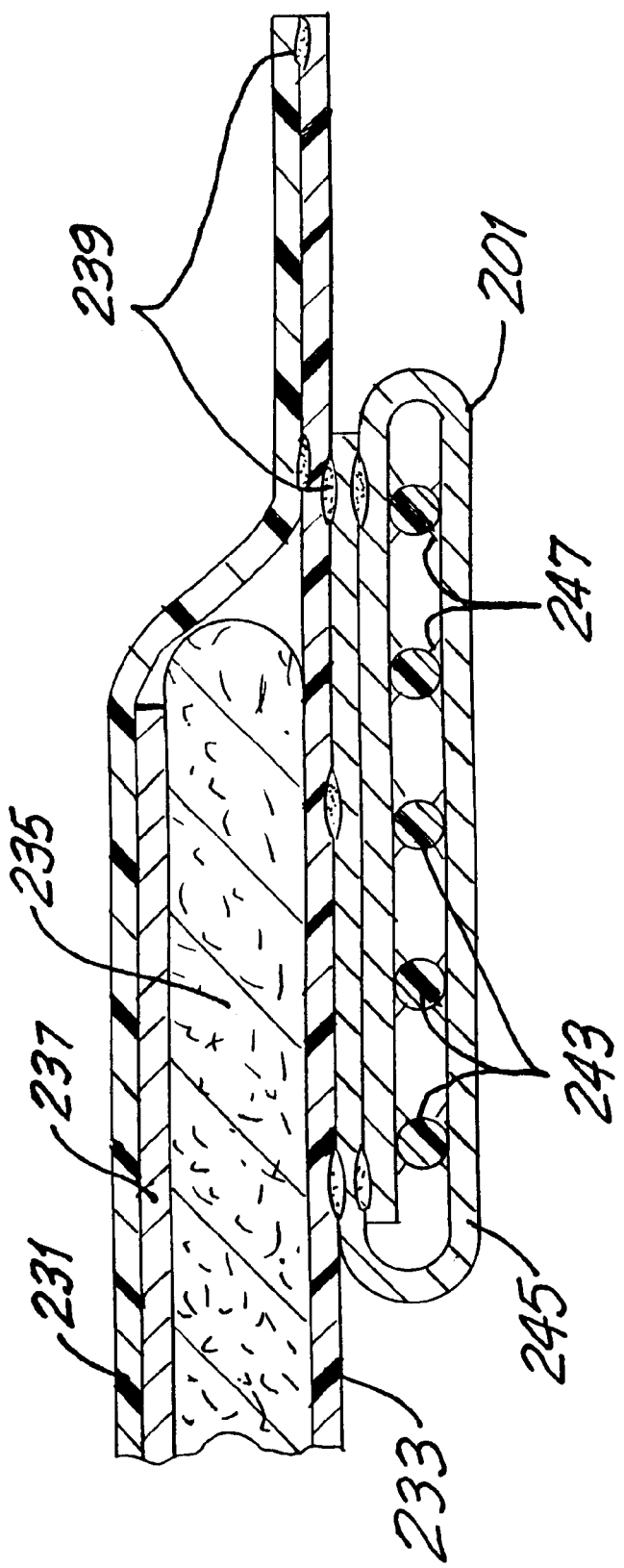
FIG. 9 is a cross sectional view taken along the line 9—9 of FIG. 7 showing the attachment of the bands to the backsheet, and further showing the relative positions of the bands and other parts of the article.

The longitudinal portion 203 has a left-hand rear band portion 209 and the longitudinal portion 205 has right-hand rear band portion 211 at the back waist region 213 of the absorbent article, and are outwardly folded at said region in a generally lateral direction along the waist as shown in FIG. 7. The left rear band portion 209 terminates in a rear closure tab 215 and the right rear band portion 211 terminates in the closure tab 217. The longitudinal left and right portions 203 and 205 are folded back at the front waist region 221 and secured at the left waist portion 223 and right waist portion 225. Alternatively, as shown in FIG. 8, the portions 203 and 205 of the elastic bands 201 may be attached unfolded at the front waist portion 227 of the absorbent article. The elastic bands 201 are securely attached to the back waist reinforcement panel or pad 229 by means of a suitable adhesive, such as construction (i.e., non-elastic) adhesive as hereinbefore mentioned in connection with description of the embodiment shown in FIGS. 1–5.

The disposable absorbent article 200 shown in FIGS. 6–9 also comprises a body side liquid pervious top sheet or layer 231 (see FIG. 9), an outer liquid impervious sheet or layer 233 and absorbent layer or pad 235 disposed between said two layers. An acquisition layer 237 is disposed between the liquid pervious top layer 231 an the absorbent layer 235. The elastic bands 201 are securely adhered to the outer side of the liquid impervious backsheet 233 by means of a suitable adhesive such as the construction adhesive 239 as in the embodiment illustrated in FIGS. 1–5.

The absorbent article 200 has a crotch region 241 which comprises the liquid pervious top layer 231, the liquid impervious backsheet or layer 233 and the absorbent layer or pad 235. The different layers are adhered to one another essentially in the same manner as described in connection with the description of FIG. 5. Each tensionable elastic band comprises the elastic elements 243 which are attached to the band wrapping material 245 by means of the elastic adhesive 247. The wrapping material 245 envelopes the elastic elements 243 and is secured against unfolding by the construction adhesive 239.

As in the previously described embodiment, the construction hot melt adhesive is applied intermittently between the liquid impervious layer 233 and the elastic bands 201 when the elastic bands are in stretched condition. When the elastic bands contract, the absorbent article is rendered elastic in the longitudinal direction between the front and back portions of the article and around the circumference of the waist.

In use, the disposable absorbent article is placed around the waist with the belts tensioned so as to fit snugly but comfortably to the shape of the wearer's body while the legs extend through the leg openings 207. The belts are then adjusted to the body shape by stretching the left hand band portion 209 and the right hand portion 211 and securing the end closure means or tabs 215 and 217 by attaching them to an attachment zone 249 by Velcro® or any suitable attachment means.

Figure 10:
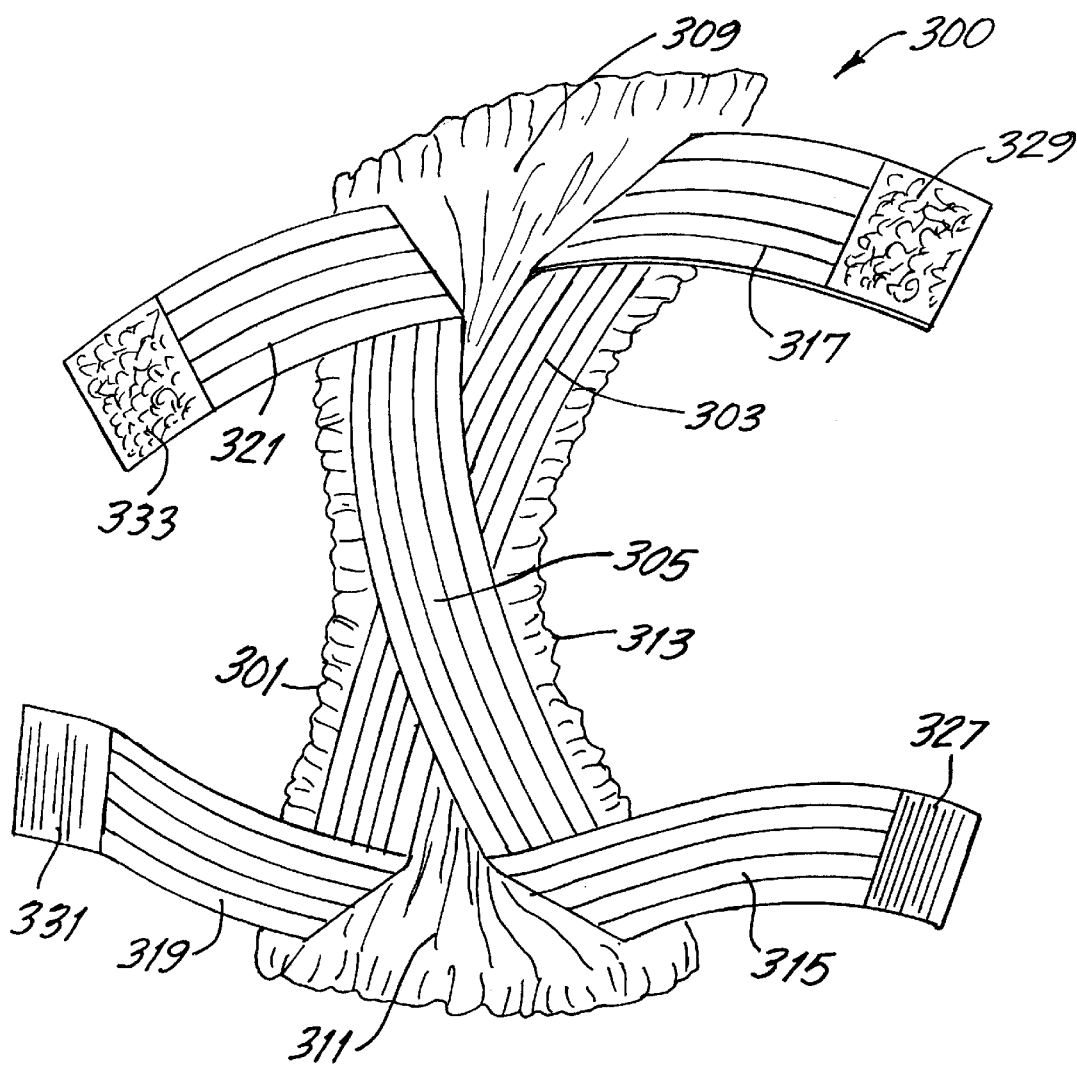
FIG. 10 is a partially perspective view of another embodiment of the present invention similar in structure to the embodiment shown in FIG. 1, but wherein the elastically contractible bands are attached to the outside of the absorbent article and cross each other in the crotch region, and closure means are disposed at the ends of the bands.
Figure 11:
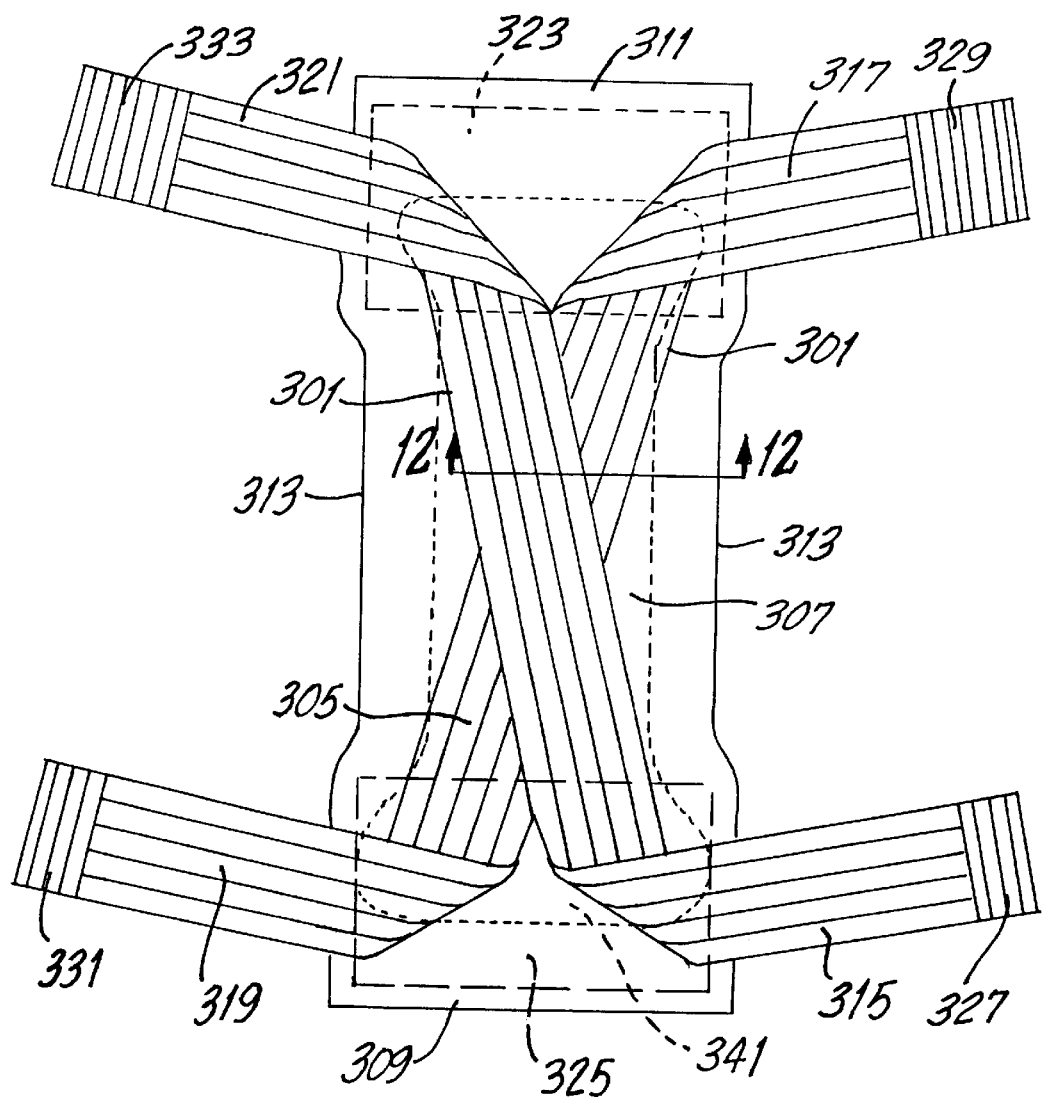
FIG. 11 is a stretched plan view of the embodiment shown in FIG. 10.
Figure 12:
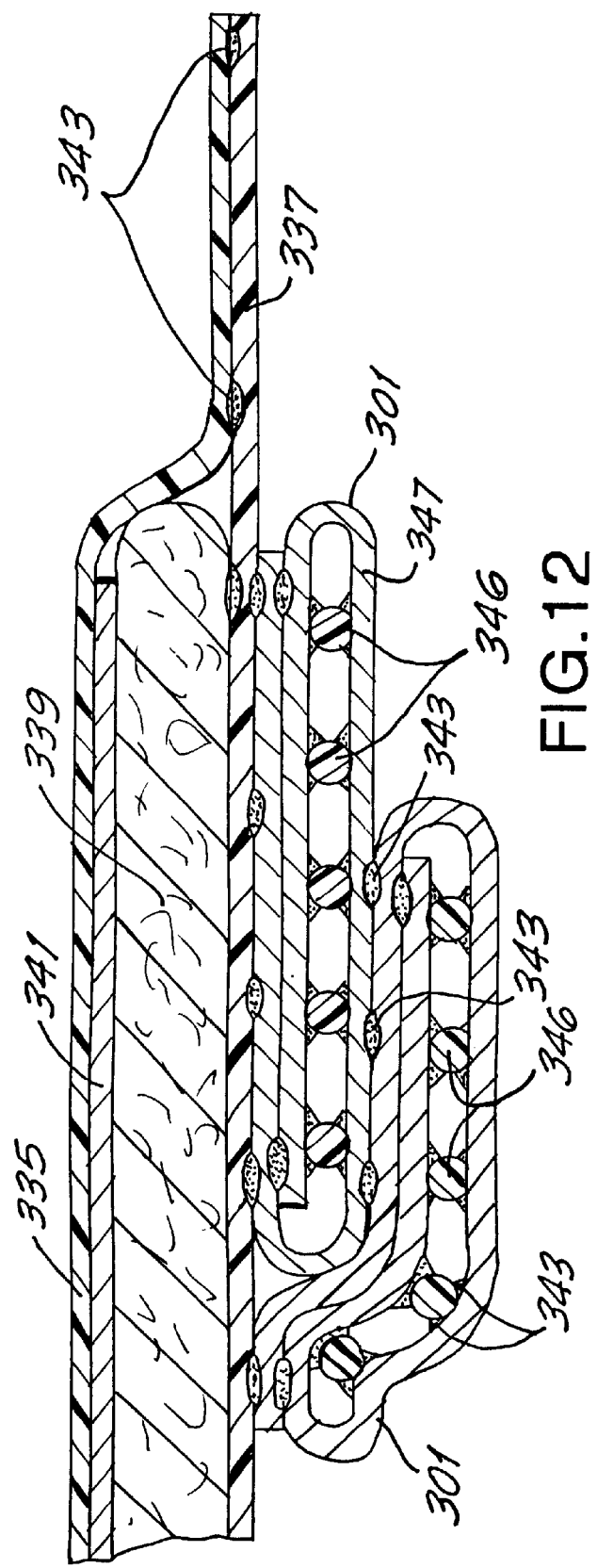
FIG. 12 is a cross sectional view taken along the line 12—12 of FIG. 11 showing the attachment of the bands to the backsheet and the relative positions of the bands and other parts of the absorbent article.

In the embodiment shown in FIGS. 10–12, inclusive, the absorbent article 300 is shown in partial perspective stretched view with emphasis on the configuration and relative positions of the elastic bands. Otherwise, the article shown therein is of the same general construction as the disposable absorbent article illustrated in FIGS. 1 and 6.

With reference to FIGS. 10, 11 and 12, the elastic bands (belts) 301 are attached to the outside of the article with the band portions 303 and 305 being disposed at an angle relative to the longitudinal axis of the article, crossing each other in the crotch region 307, thus forming a generally V-shaped configuration in the front waist portion 309 and back waist portion 311 of the article. By positioning the elastic belts 301 near the leg openings 313 of the absorbent article, an elastic gasketing seal is formed around the leg openings.

The diagonally disposed band portions 303 and 305 of the belts are folded outwardly as shown by the left hand back band portion 315, the left hand front band portion 317, the right hand back band portion 319 and the right hand front band portion 321. The elastic belts 301 are securely fastened at the front waist reinforcement panel 323 and the back reinforcement panel 325 by means of a suitable adhesive such as the construction adhesive as hereinbefore described. The left rear band 315 terminates in the closure means or end tab 327, the left-hand front band 317 terminates in the closure means or end tab 329, the right hand rear band 319 terminates in the closure means or end tab 331 and the right hand front band 321 terminates in the end tab 333.

As in the case of the two previously described embodiments, the disposable absorbent article shown in FIGS. 10–12 comprises a body-side liquid pervious top cover 335, an outer liquid impervious backsheet or layer 337 and an absorbent layer 339 disposed therebetween (see FIG. 12). An acquisition layer 341 is placed between the absorbent layer 339 and the liquid pervious layer 335. The two elastic bands 301 are secured to the outer side of the liquid impervious layer 337 by means of a suitable adhesive, such as the construction hot melt adhesive 343. The construction adhesive 343 is applied intermittently between the liquid impervious layer 337 and the elastic belts 301 while the belts are in stretched condition. When the belts contract, the absorbent article 300 is rendered elastic in the longitudinal direction between the front and back portions of the article and around the circumference of the waist. As is further shown in FIG. 12, the belts 301 of absorbent article 300 are provided with the tensionable elastic elements 346 which are attached to the band wrapping material 347 by means of the adhesive 343.

In use, the absorbent article is placed around the waist and is adjusted to the wearer's body shape by stretching the belts 301 and securing them through engagement of the end closure tabs such that the closure tab 327 is engaged with the closure tab 329, and the closure tab 331 is engaged with the closure tab 333 by Velcro® or any other suitable securing means.

Figure 6:
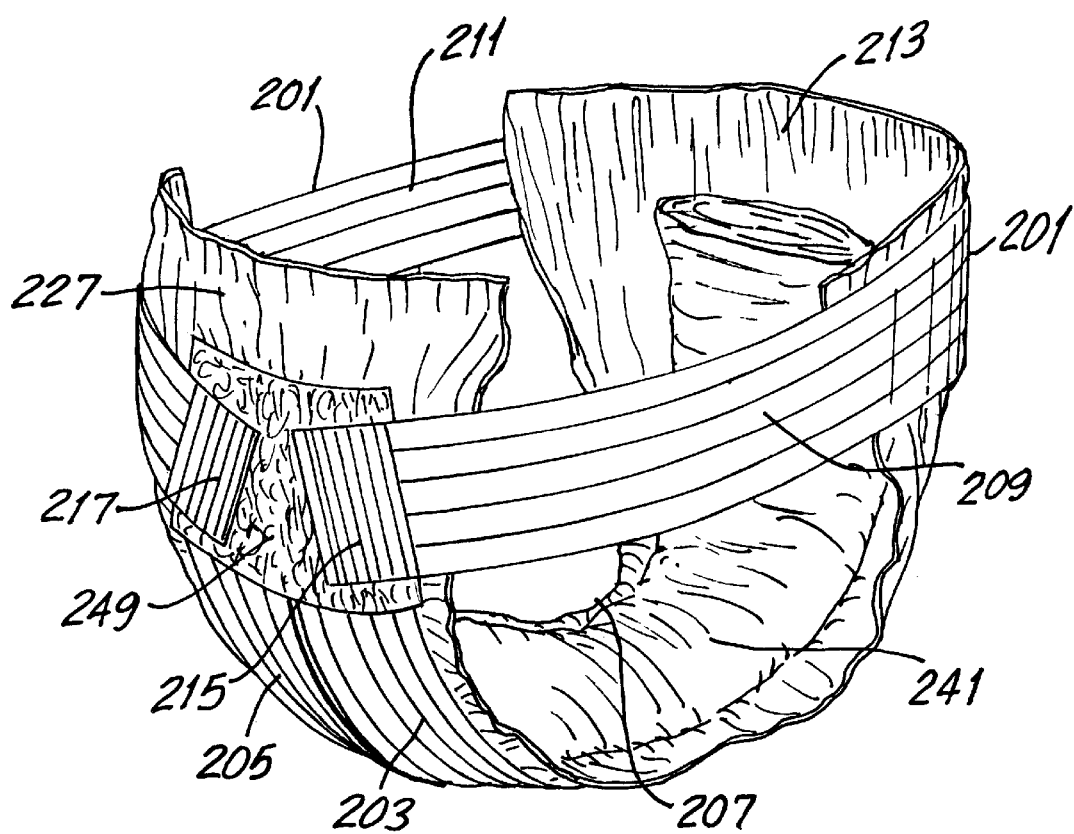
FIG. 6 is a perspective view of another embodiment of the invention substantially similar in construction to FIG. 1, but wherein the elastically contractible bands are attached to the outer side of the backsheet and the closure means is located at the front of the waist portion of the absorbent article.
Figure 13:
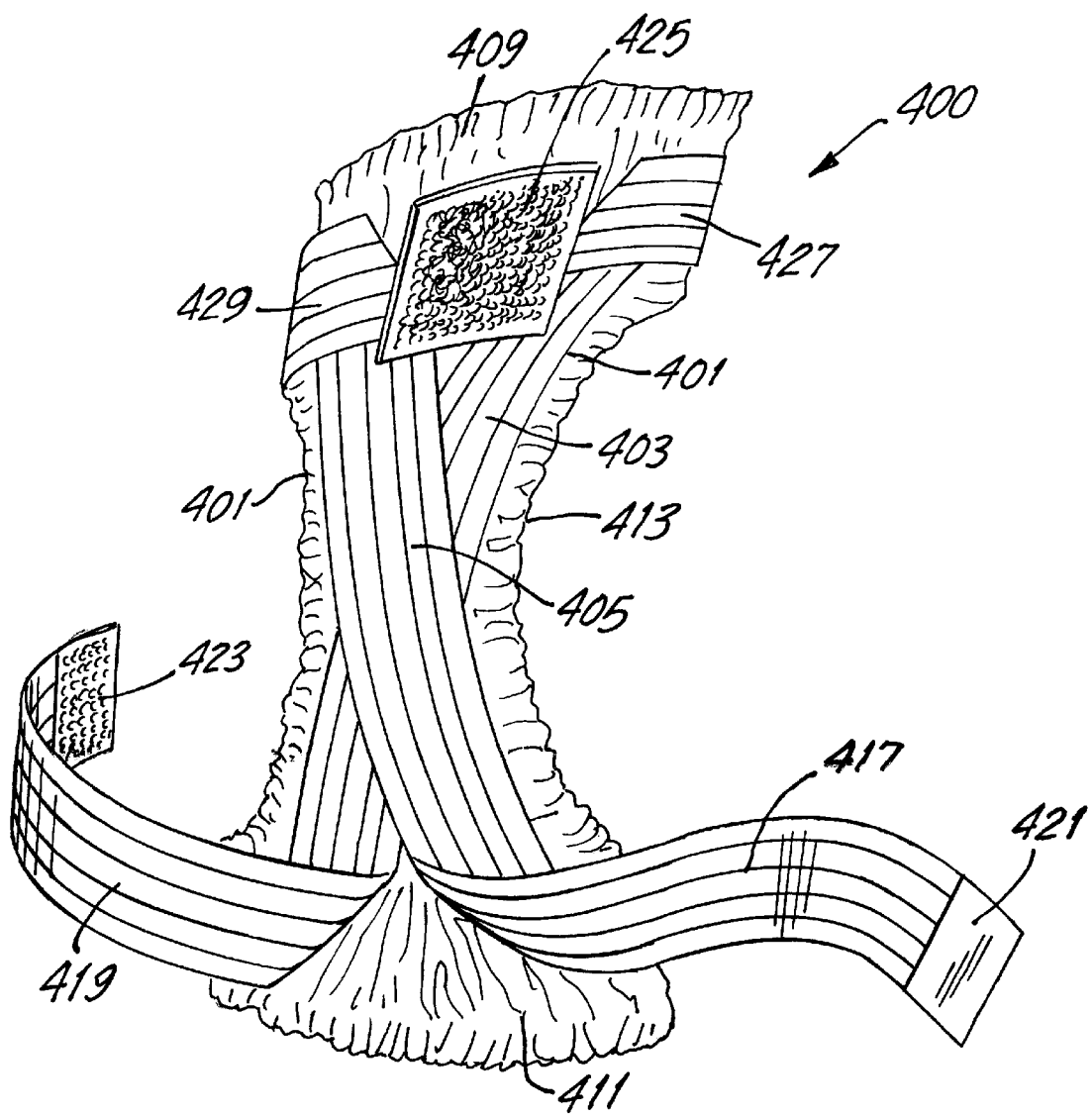
FIG. 13 is a partially perspective view of another embodiment of the present invention similar in structure to the embodiment shown in FIG. 10, but wherein the elastically contractible bands are attached to the outside of the absorbent article and cross each other in the crotch region, and the closure means are disposed in the front waist portion of the article.
Figure 14:
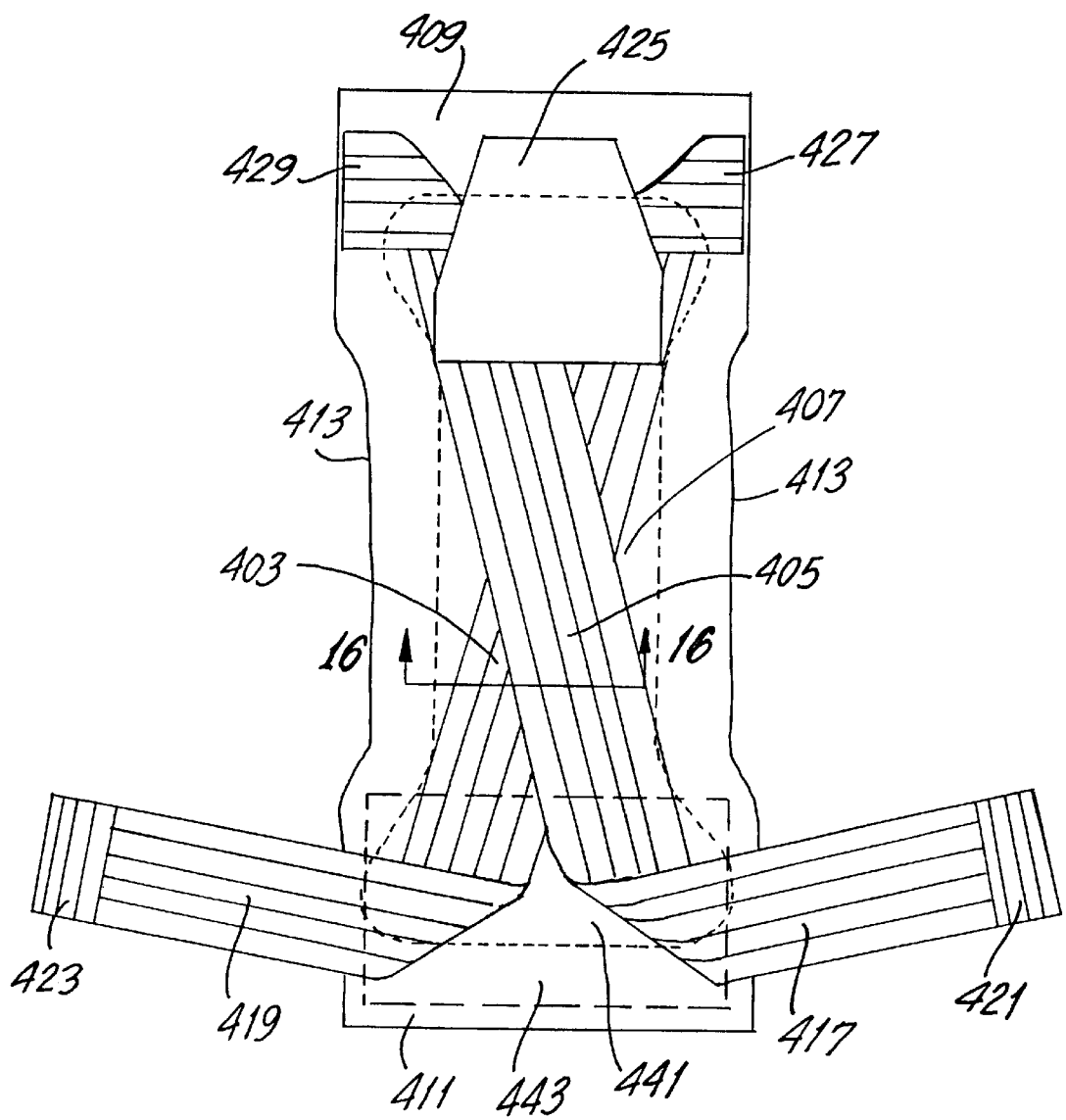
FIG. 14 is a stretched plan view of the embodiment shown in FIG. 13 wherein the front side ends of the bands are folded towards the waist.
Figure 15:
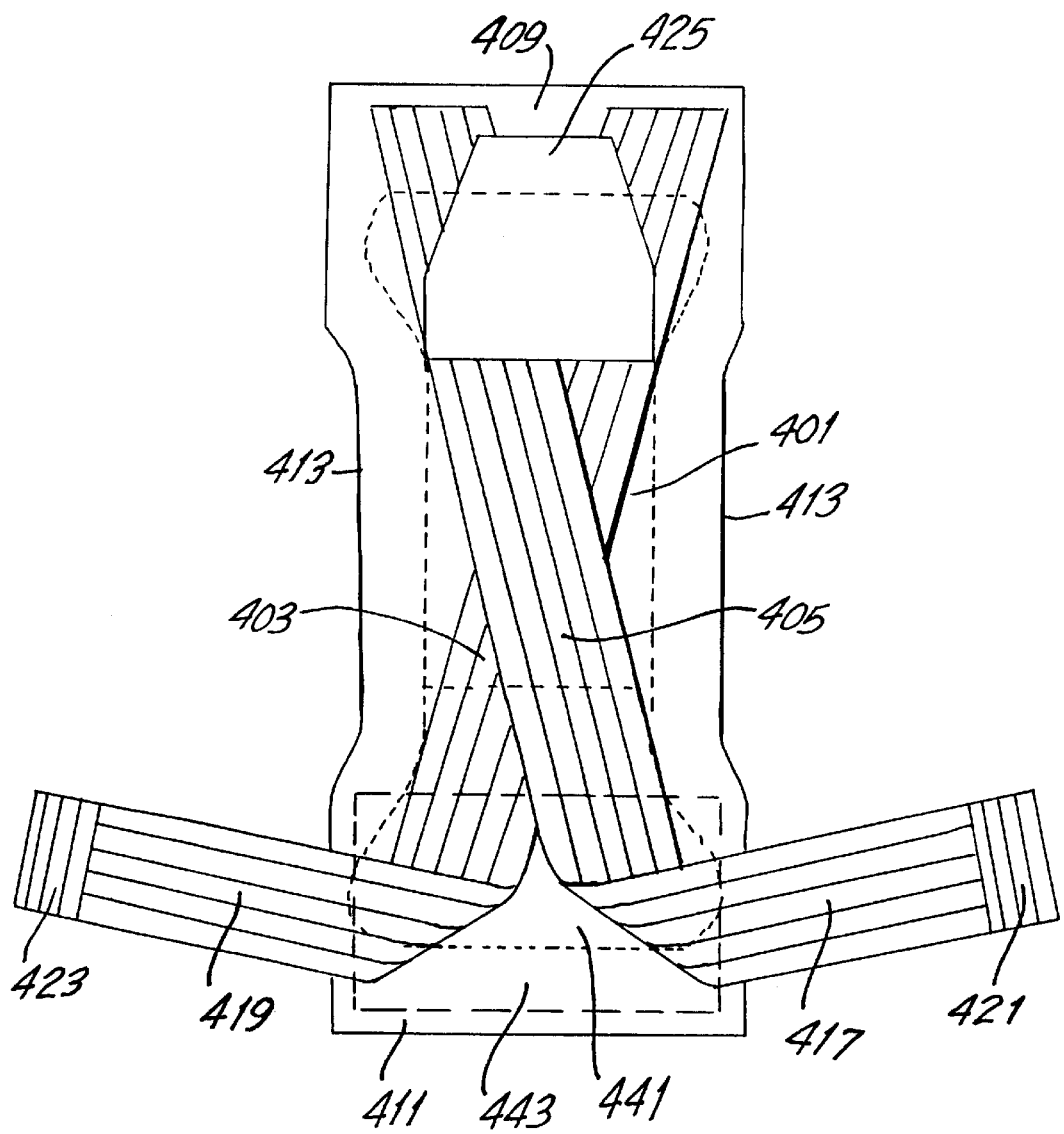
FIG. 15 is a stretched plan view of the embodiment shown in FIG. 13 but wherein the front side ends of the bands terminate at the waist.

Referring to FIGS. 13–16, inclusive, the absorbent article generally designated as 400 in FIG. 13 has the same general construction as the absorbent article shown in FIG. 6. Once again, however, this figure is shown in stretched view as the embodiment shown in FIG. 10. Thus, the absorbent article 400 in FIG. 13 comprises the elastic tensionable belts 401 comprising an inner longitudinal band portion 403 and an outer longitudinal band portion 405 which cross each other at the crotch region 407, at an acute angle relative to the longitudinal axis of the absorbent article, forming a generally V-shaped configuration at the crotch region in the front waist portion 409 and the back waist portion 411 of the article. By positioning the elastic belts 401 near the leg openings 413, an elastic gasketing seal is formed around each leg opening. The left hand inner longitudinal band portion 403 and right hand outer longitudinal band portion 405 are folded outwardly in the waist region into the lateral directions to form the left hand rear band portion 417 and the right hand rear band portion 419. The left hand rear band portion 417 terminates in the end closure tab 421 and the right hand rear band portion 419 terminates in the end closure tab 423. In the front portion, the absorbent article is provided with a Velcro covered attachment region 425 for attachment thereto of the front ends of the folded closure tabs 427 and 429 of the longitudinal band portions 405 and 403 (see FIG. 14). Alternatively, as shown in FIG. 15, these front end portions of the belts may be attached unfolded to the attachment region 425.

Figure 16:
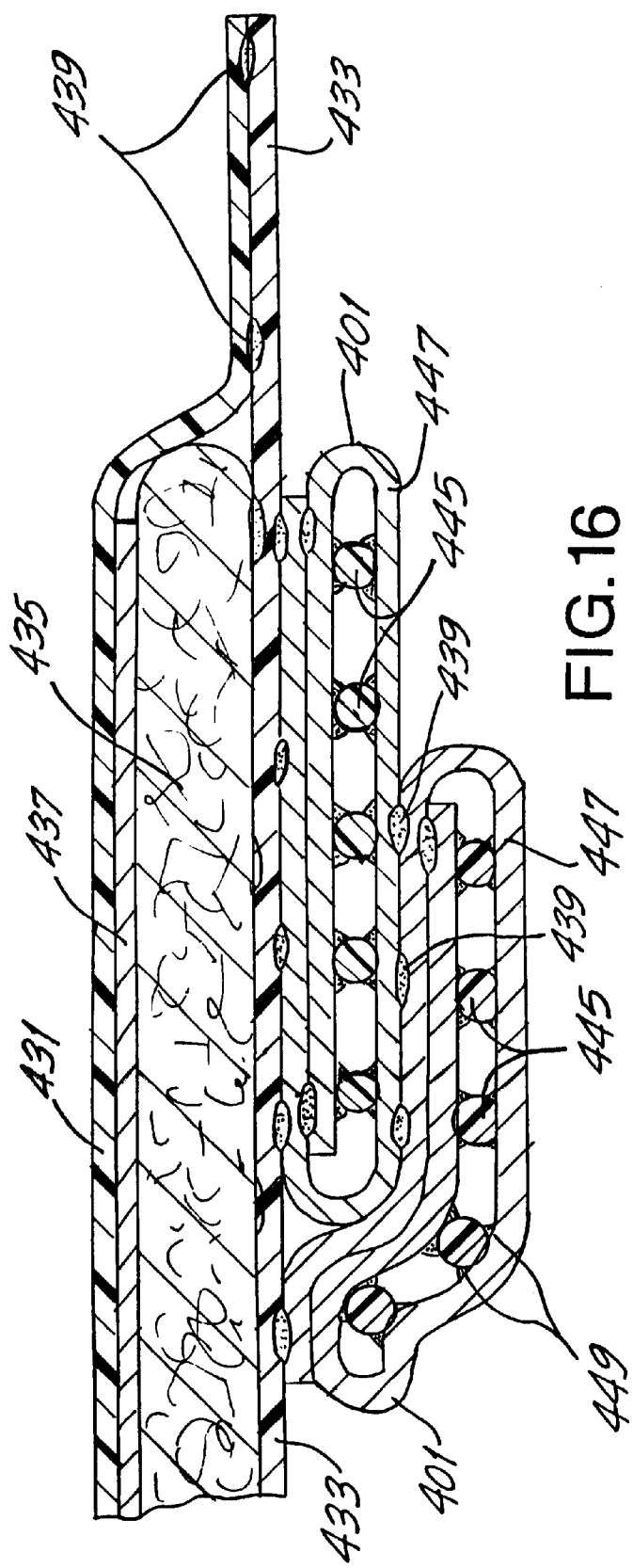
FIG. 16 is a cross sectional view taken along the line 16—16 of FIG. 14 showing the attachment of the bands to the backsheet and also showing the relative positions of the bands and other parts of the articles.

The disposable article 400 also comprises a body side liquid pervious top sheet or layer 431, an outer impervious backsheet or layer 433 and an absorbent core layer 435 disposed between said two layers. As in the pervious embodiments, an acquisition layer 437 is placed between the absorbent core layer 435 and the liquid pervious layer 431 as shown in FIG. 16 and the layers are sealed to form a composite sheet. The elastic belts 401 are attached to the outer side of the liquid impervious backsheet 433 by means of the construction hot melt adhesive 439. As in the previous embodiments, the construction hot melt adhesive 439 may be applied intermittently between the liquid impervious backsheet 433 and the elastic belts 401 while the belts are in stretched condition. Thus when the elastic bands 401 contract, the absorbent article 400 will be rendered elastic in the longitudinal direction between the front and back portions of the absorbent article. Also as in the previous embodiments, the absorbent article 401 comprises absorbent pad 441 and the back reinforcement pad 443. The elastic belts 401 are provided with the tensionable elastic elements 445 which are attached to the band wrapping material 447 by means of the elastic adhesive 449.

In use, the disposable article is placed around the waist and is adjusted to the body shape by stretching the elastic band portions 403 and 405 and securing them in place by engaging the end closure tabs 421 and 423 and attaching the ends 427, 429 to the attachment region 425.

Figure 17:
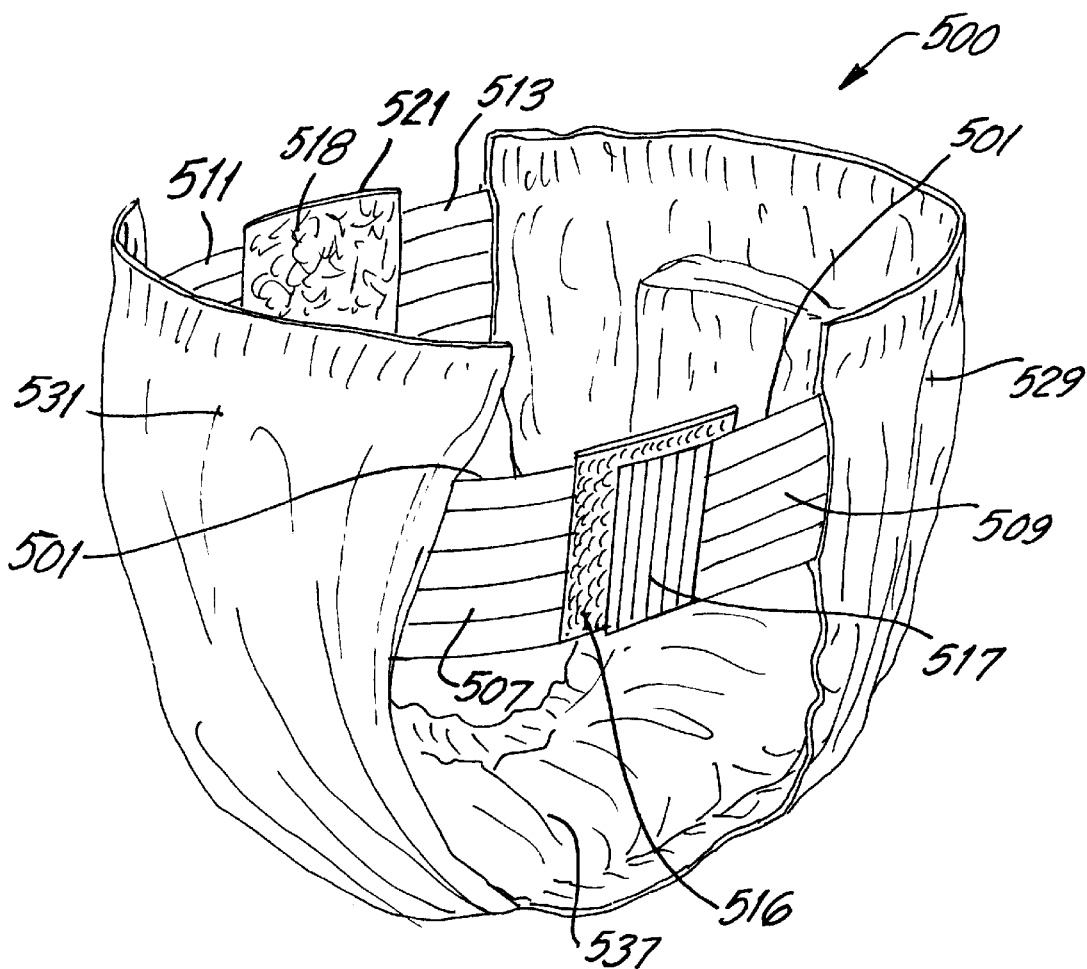
FIG. 17 is a perspective view of another embodiment of the present invention similar in structure to the embodiment shown in FIG. 1, but wherein the elastically contractible bands are attached to the inner side of the backsheet and the closure means are located at the ends of the bands.
Figure 18:
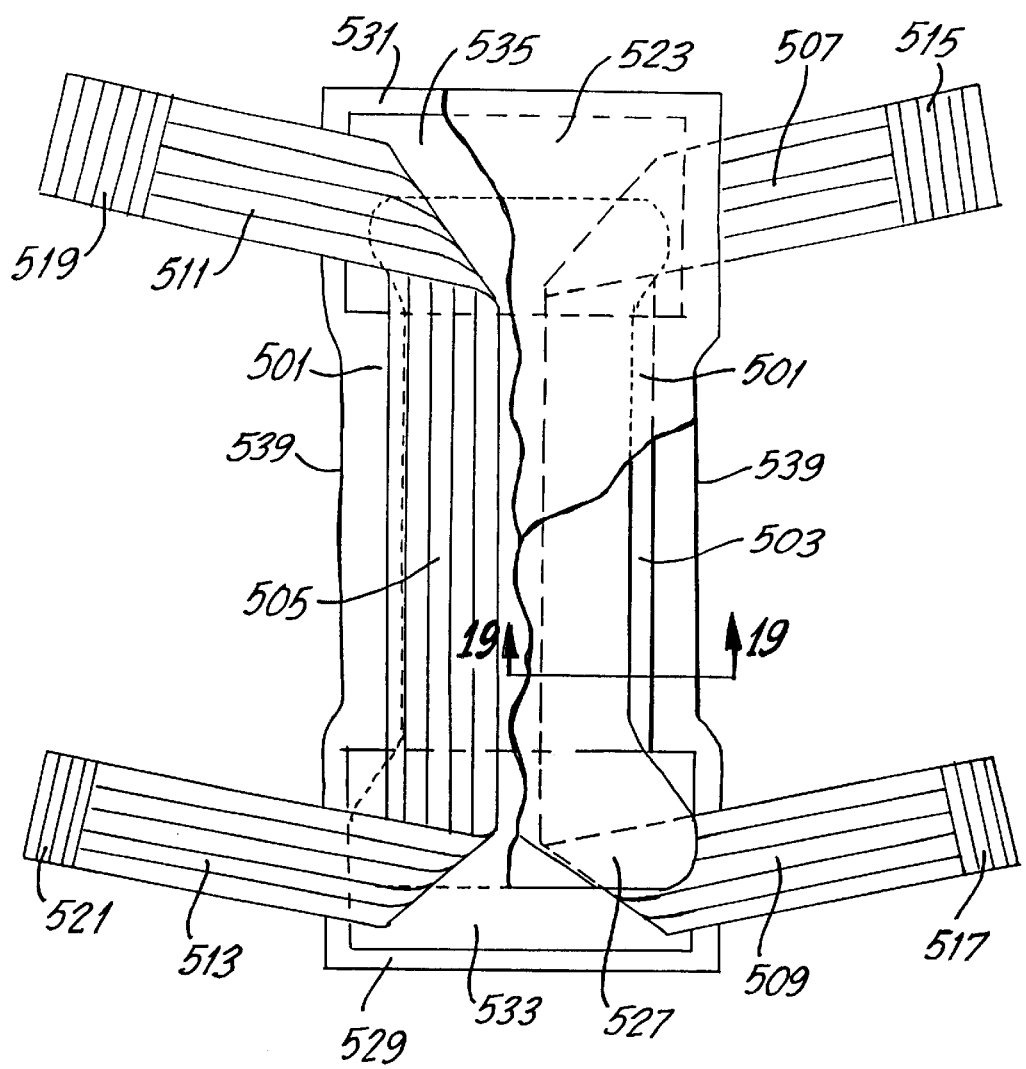
FIG. 18 is a plan view of the embodiment shown in FIG. 17, in stretched position.
Figure 19:
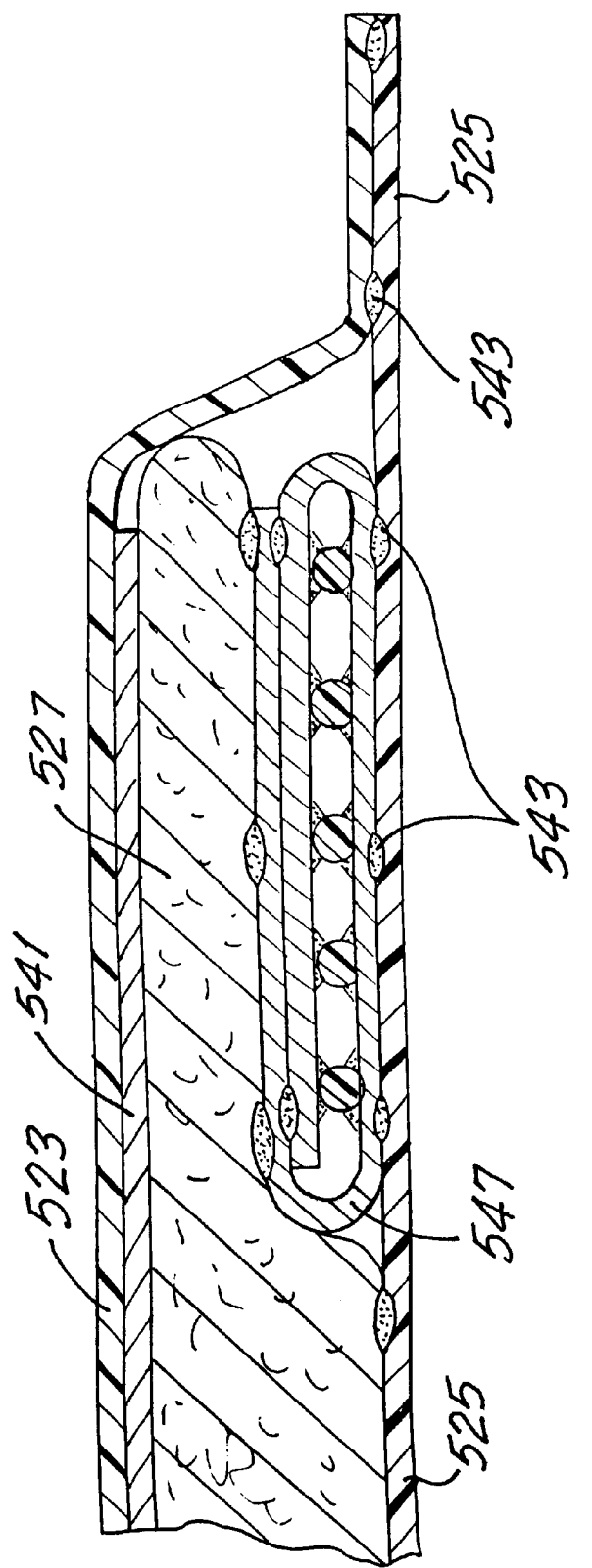
FIG. 19 is a cross sectional view taken along the line 19—19 in FIG. 18 showing the attachment of the bands to the backsheet and the closure means in the front of the waist portion of the absorbent article.
Figure 20:
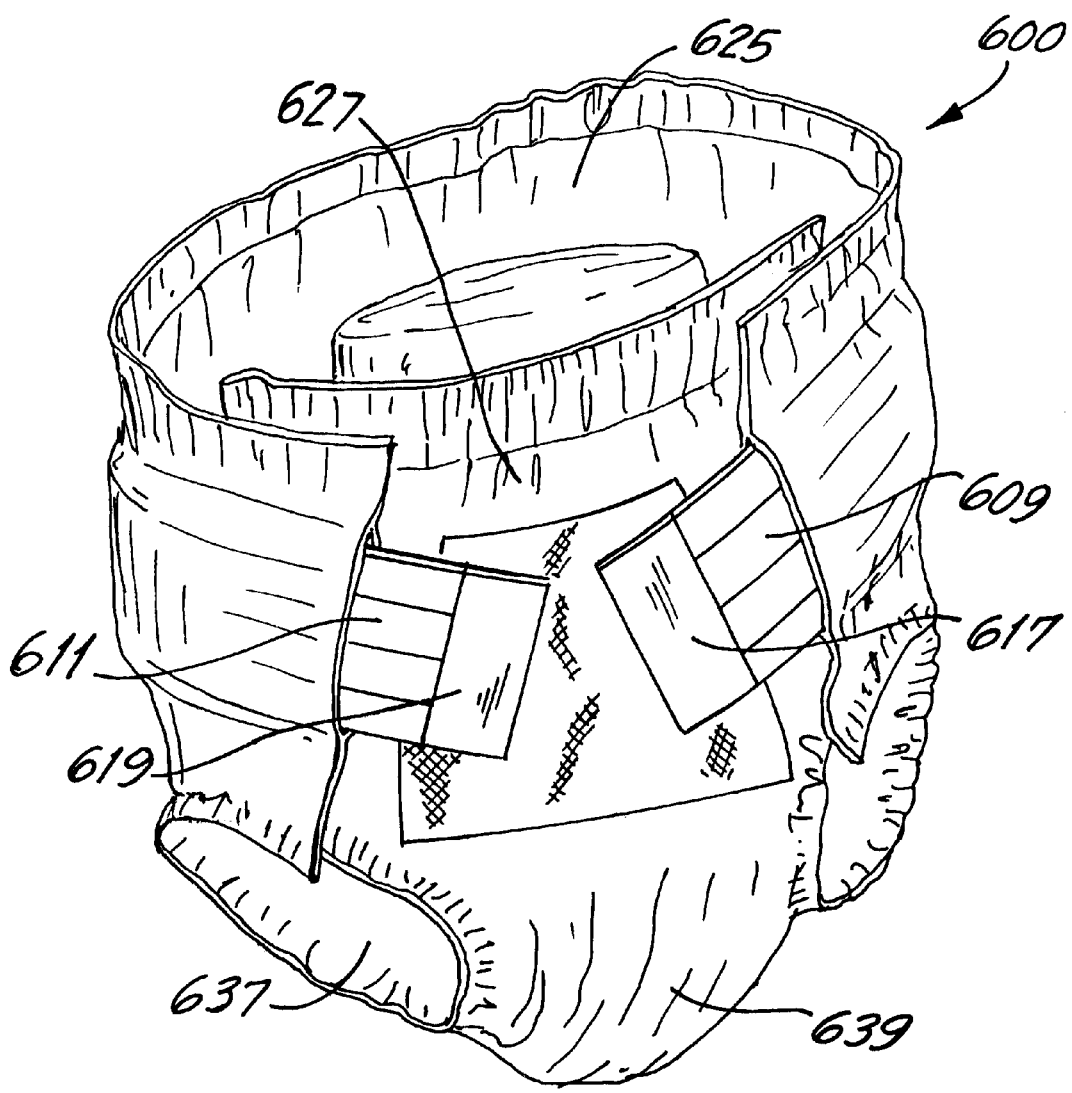
FIG. 20 is a perspective view of another embodiment of the present invention similar in structure to the embodiment shown in FIG. 6, but wherein the elastically contractible bands are attached to the inside of the backsheet, and the closure means are located in the front of the waist portion of the absorbent article.
Figure 21:
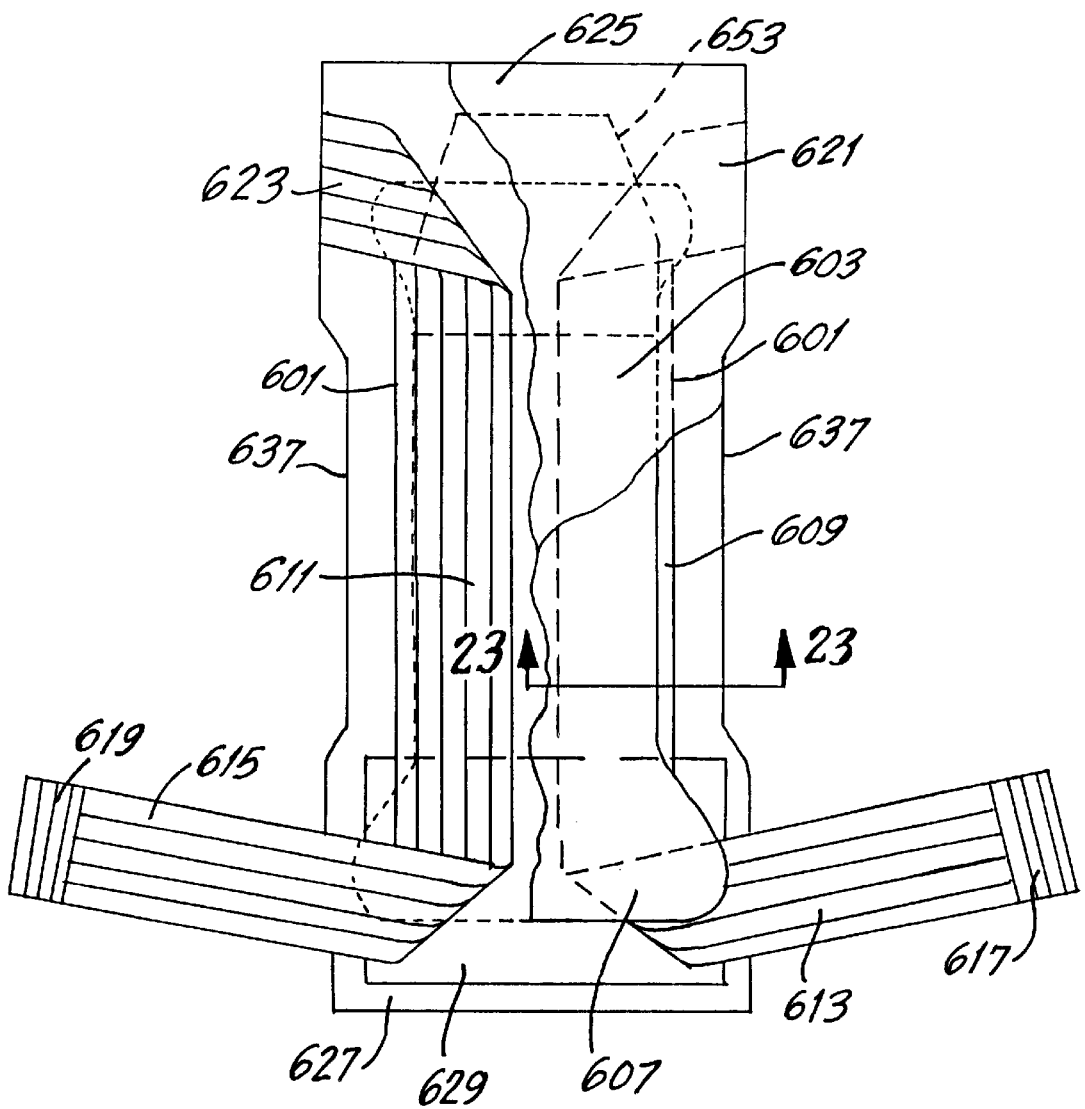
FIG. 21 is a stretched plan view of the embodiment shown in FIG. 20 wherein the front side ends of the bands are folded towards the waist.
Figure 22:
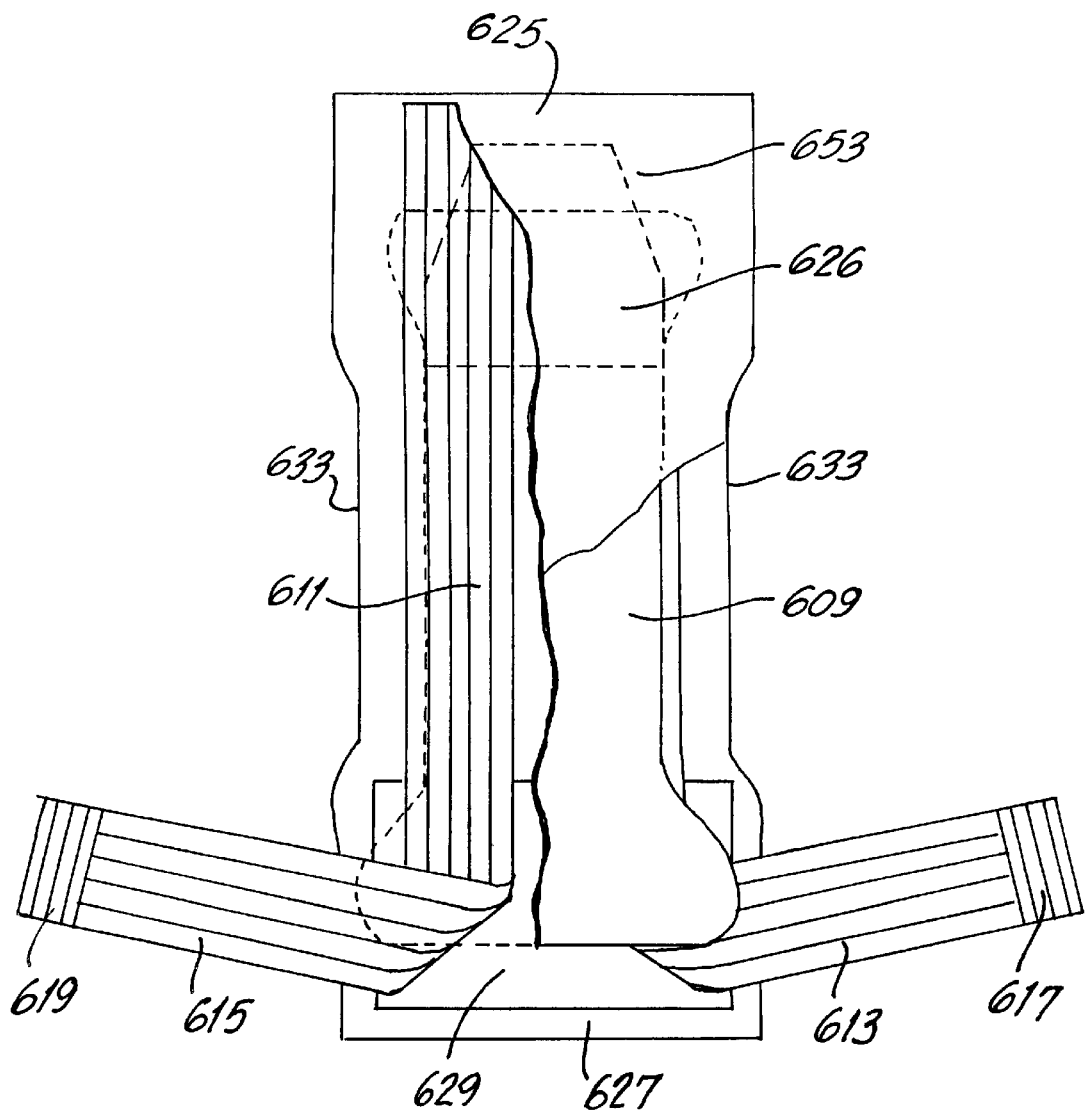
FIG. 22 is a stretched plan view of the embodiment shown in FIG. 20 wherein the front side ends of the bands terminate at the waist.

In the embodiment illustrated in FIGS. 17–19, inclusive, the elastic belts are attached to the inner side of the absorbent article. Thus, as is shown in FIG. 17, the absorbent article 500 is of the same general construction as the article shown in FIG. 1 and comprises the elastic tensionable belts 501 having a right hand longitudinal band portion 503 and a left hand longitudinal band portion 505, both disposed generally parallel to the longitudinal axis of the absorbent article 500. The right hand band portion 503 is folded laterally outwardly into a right hand front band portion 507 and in the rear into a right hand rear band portion 509. Similarly, the left hand band portion 505 is folded laterally outward into a left hand front band portion 511 and in the rear into a left hand rear band portion 513. Each of the lateral band portions 507, 509, 511 and 513 terminate in an end closure tab 515, 517, 519 and 521, respectively.

The absorbent article 500 comprises a liquid permeable layer or cover 523 facing the body of the wearer, a liquid impervious layer or backsheet 525 and an absorbent layer or pad 527 therebetween. The elastic bands 501 are fastened to a front waist reinforcement pad 535 and are disposed between the inner surface of the liquid impervious backsheet 525 and the absorbent pad 527. The absorbent article 501 also comprises back waist portion 529, the front waist portion 531, a back waist reinforcement pad 533, a front waist reinforced pad 535, a crotch region 537 and leg openings 539. When the elastic belts 501 are placed near the leg openings 539, they form an elastic gasketing seal around the leg openings.

Referring to FIG. 19, there is shown an acquisition layer 541 between the liquid pervious layer 523 and the liquid impervious backsheet or layer 525. Two elastic belts 501 are attached to the outer side of the liquid impervious backsheet 525 by means of the construction hot melt adhesive 543, which may be applied intermittently between the liquid impervious layer 525 and the elastic belts 501 when the belts are in stretched condition. The elastic belts 501 comprise the tensionable elastic elements 545 which are attached to the wrapping material 547 by means of the adhesive 543. Thus, once again as described in connection with the previous embodiments, when the belts 501 contract, the absorbent article is rendered elastic in the longitudinal direction between the front and back portions of the absorbent article and along the circumference of the waist.

In use, the disposable article is placed around the waist of the wearer and is adjusted to the wearer's body shape by stretching the elastic bands and securing them by engaging the end closure tabs 515, 517, 519 and 521, at the attachment portions 516 and 518, respectively.

Figure 23:
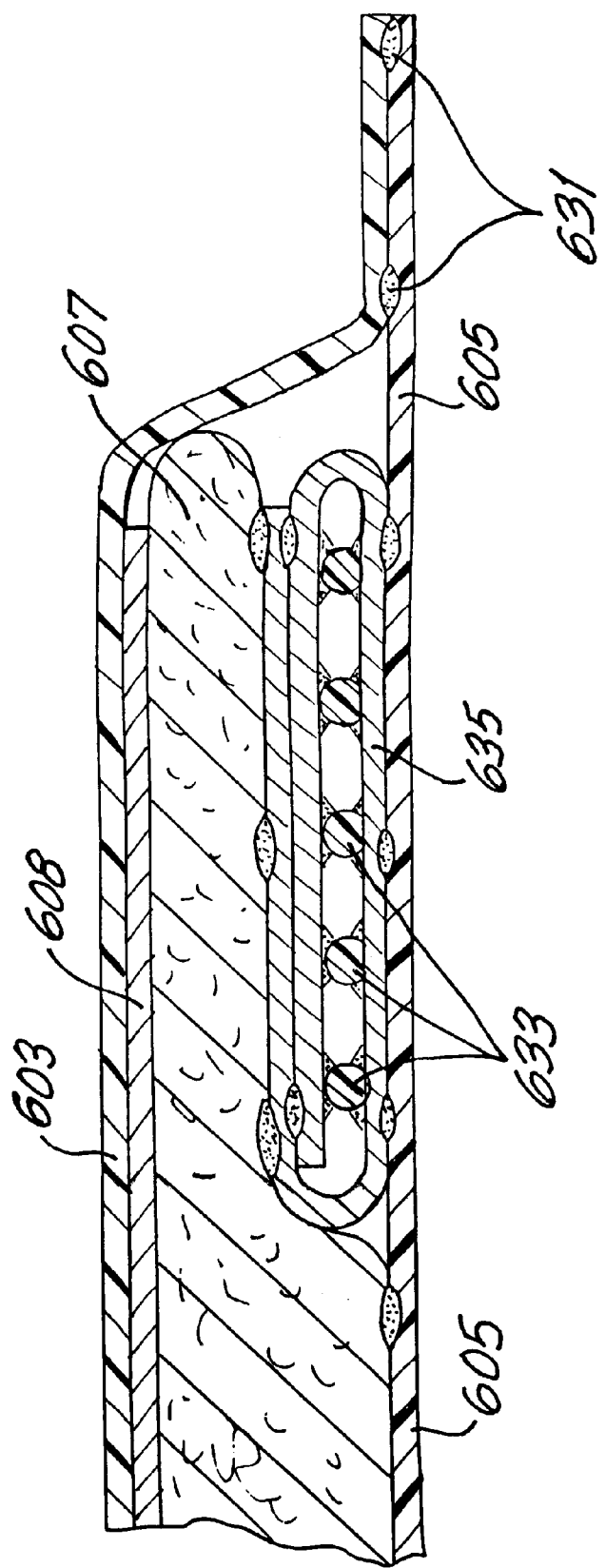
FIG. 23 is a cross sectional view taken along the line 23—23 in FIG. 20 showing the attachment of the bands to the backsheet, and the relative positions of the bands and other components of the article.

In the embodiment shown in FIGS. 20–23, the disposable absorbent article generally designated as 600 comprises the elastic tensionable belts 601 attached to the inner side of the article as hereinafter described. The absorbent article 600 comprises a liquid pervious layer 603 facing the wearer's body, a liquid impervious layer or backsheet 605 superimposed on the liquid pervious layer 603 and an absorbent pad or layer 607 disposed therebetween. An acquisition layer 608 is placed between the absorbent layer 607 and the liquid pervious layer 603 as shown in FIG. 23. As in the previous embodiments, these layers are sealed at these ends to form a composite sheet.

The elastic tensionable belts 601 are positioned to the left and right of the longitudinal axis of the article in generally parallel relation thereto, and comprise the right hand longitudinal band portion 609 and the left hand longitudinal band portion 611. In the back portion of the absorbent article 600, the right hand band portion 609 is folded laterally outward into the right hand lateral band portion 613 and the left hand band portion 611 is folded laterally outward into the left hand lateral band portion 615. The right hand lateral band portion 613 terminates in the closure tab 617 and the left hand lateral band portion 615 terminates in the closure tab 619. In the front portion of the article, the right hand longitudinal band portion 609 is folded laterally outward into the band portion 621 and the left hand longitudinal band portion 611 folds laterally outward into the band portion 623. The laterally folded portions 621 and 623 may be attached at the front waist portion 625 (see FIG. 21) or they may be attached unfolded at the front waist portion 625 (see FIG. 22). The back waist portion 627 of the absorbent article is provided with a back reinforcement pad 629. The elastic bands 601 are fastened to the back waist reinforcement pad 629 by the construction adhesive 631 and are thus attached to the inner side of the absorbent article between the inner surface of the liquid impervious backsheet 605 and the absorbent pad or layer 607. As shown in FIG. 23, the elastic bands 601 comprise the elastic elements 633 which are attached to the wrapping material 635 by means of the construction adhesive 631. By placing the elastic bands 601 near the leg openings 637, there are formed elastic gasketing seals around the legs' openings near the crotch region 639.

In use the absorbent article 600 is placed around the waist of the wearer and is adjusted to fit the body shape by stretching the left hand band portion 615 and the right hand band portion 613 and securing them by engaging the end closure tabs 617 and 619 onto the attachment zone 653.

Figure 24:
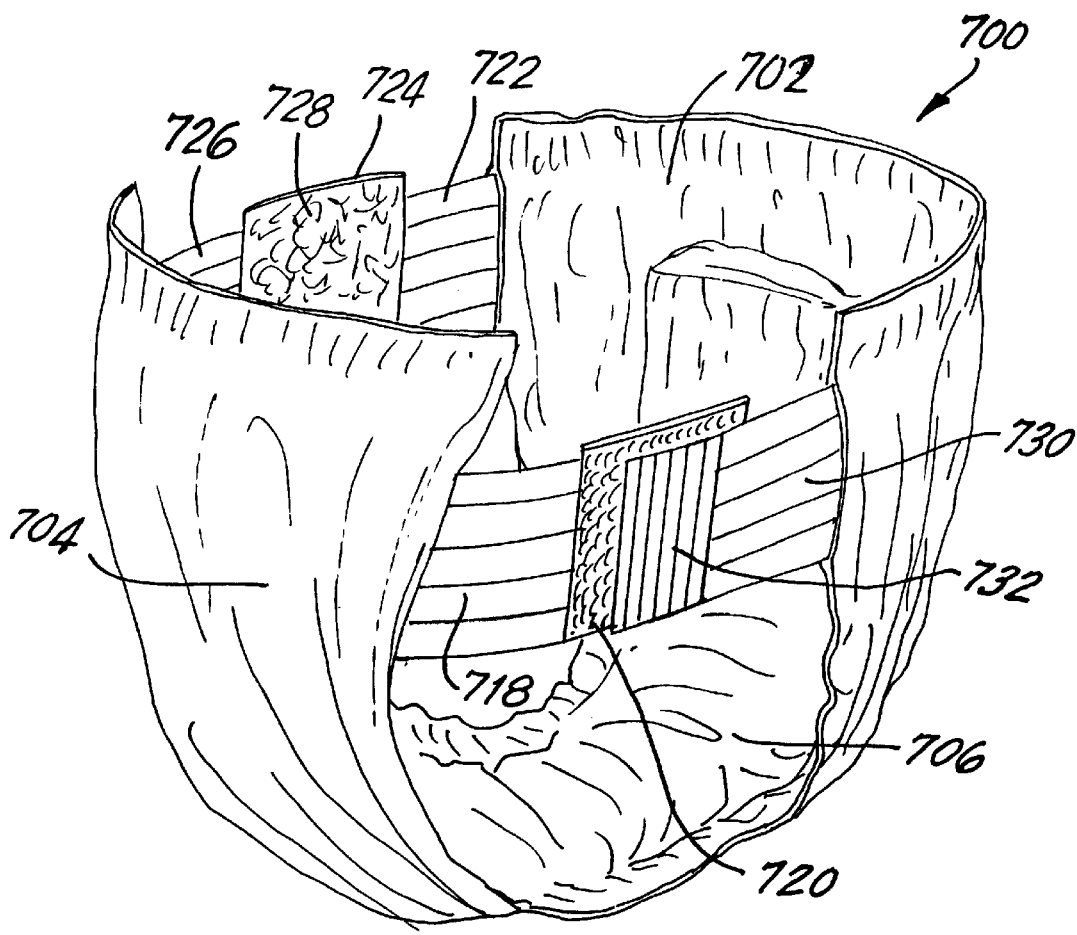
FIG. 24 is a perspective view of another embodiment of the invention similar to the embodiment shown in FIG. 1, but wherein the elastically contractible bands are attached to the inner side of the article and cross each other in the crotch region, and the closure means are located at the ends of the bands.
Figure 25:
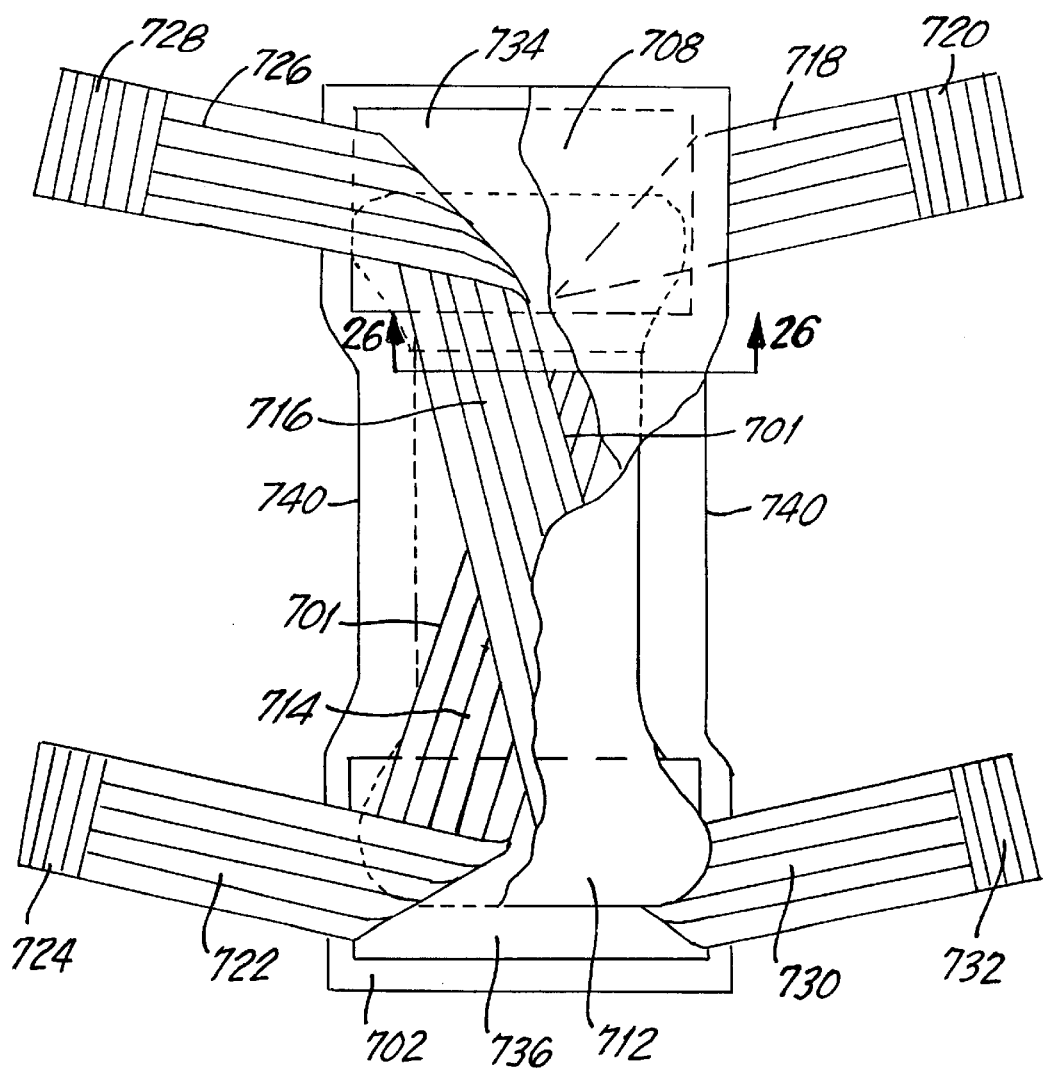
FIG. 25 is a stretched plan view of the embodiment shown in FIG. 24.
Figure 26:
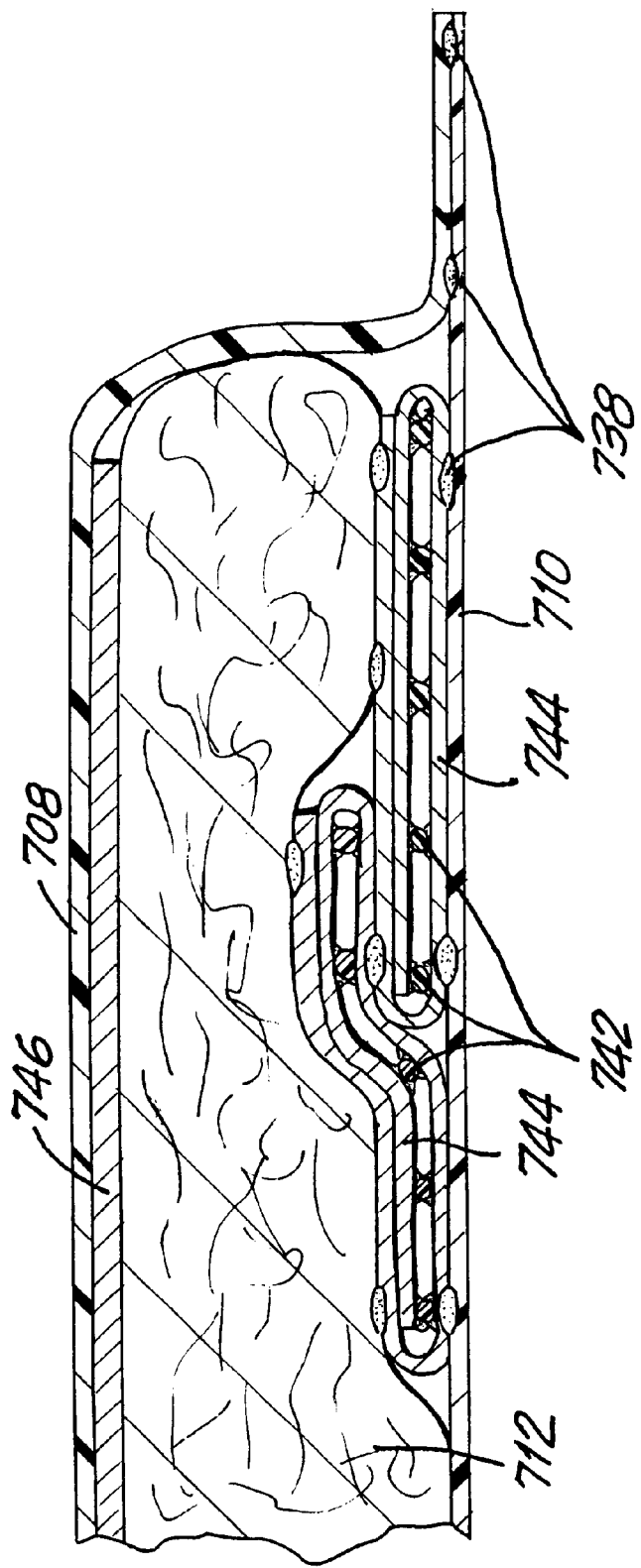
FIG. 26 is a cross sectional view taken along the line 26—26 in FIG. 24 showing the attachment of the bands to the backsheet, and the relative position of the bands and other components of the article.
Figure 27:
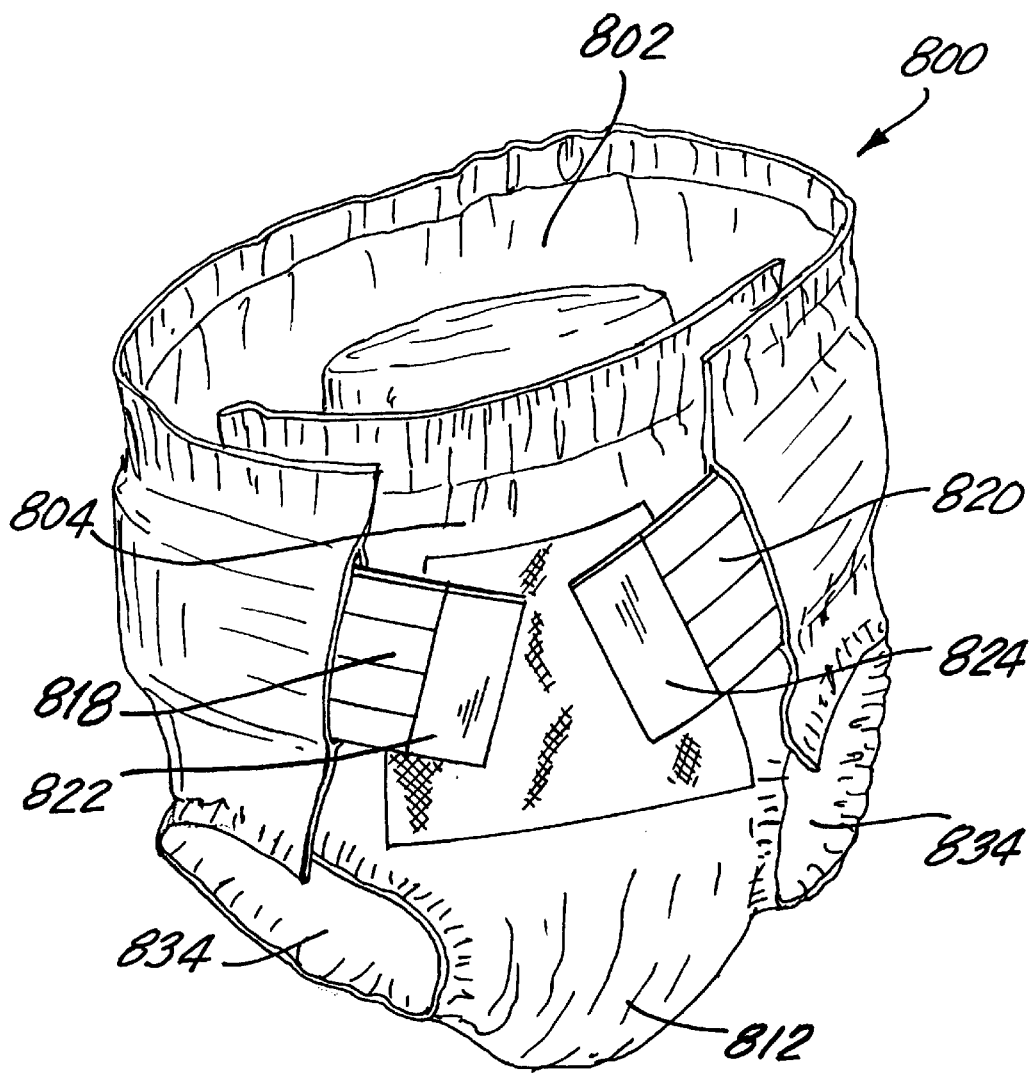
FIG. 27 is a perspective view of another embodiment of the invention similar to the structure of the embodiment shown in FIG. 6, but wherein the elastically contractible bands are attached to the inner side of the article and cross each other in the crotch region, and the closure means are located at the front waist portion of the article.

In the embodiment illustrated by FIGS. 24–26, inclusive, the absorbent article 700 comprises a back waist portion 702, a front waist portion 704, a crotch region 706, a liquid pervious layer 708 facing the body of the wearer, a liquid impervious layer or backsheet 710 and an absorbent pad or layer 712 disposed therebetween. The absorbent article 700 also comprises elastic belts 701 disposed on the left and right of the longitudinal axis of the article. Thus, the left belt 701 comprises the longitudinal diagonally disposed inner band portion 714 and the longitudinal diagonally disposed outer band portion 716. The diagonally disposed inner and outer band portions 714 and 716 cross each other at the crotch region 706 to form a generally V-shaped configuration as shown in FIG. 25. The inner band portion 714 is folded outwardly in the front portion of the article into the band portion 718 which terminates in the closure tab 720, and is folded outwardly in the back portion of the article into the band portion 722 which terminates in the closure tab 724. Similarly, the external band portion 716 is folded outwardly in the front portion of the absorbent article into the band portion 726 which terminates in the closure tab 728, and in the rear of the article is folded outwardly into the band portion 730 which terminates in the closure tab 132. The elastic belts 701 are attached to the inner side of the absorbent article and are fastened to the front reinforcement pad 734 and the back reinforcement pad 736 by means of the construction hot melt adhesive 738 (as shown in FIG. 26). As is also shown in FIG. 26, the elastic belts 701 are attached to the inner side of the liquid impervious backsheet 710 by means of the construction hot melt adhesive 738. The adhesive is applied intermittently between the liquid impervious backsheet 710 and the elastic belts 701 when the elastic bands are in stretched condition. Thus, when the bands contract, the absorbent article is rendered elastic in the longitudinal direction between the front and back portions of the article and around the circumference of the waist portion. Once again by placing the elastic belts near the leg openings 740 a gasketing seal is formed around each leg opening.

As shown in FIG. 26, the elastic bands 701 are provided with the elastic elements 742 which are attached to the band wrapping material 744 by means of the adhesive 738. An acquisition layer 746 is disposed between the liquid pervious layer 708 and the absorbent pad 712.

In use, the absorbent article 700 is placed around the wearer and is adjusted to fit the wearer's body by stretching the elastic bands 701 and securing the belts in place by attaching the closure tabs 720 and 732 together as well as engaging the closure tab 724 to closure tab 728.

Figure 28:
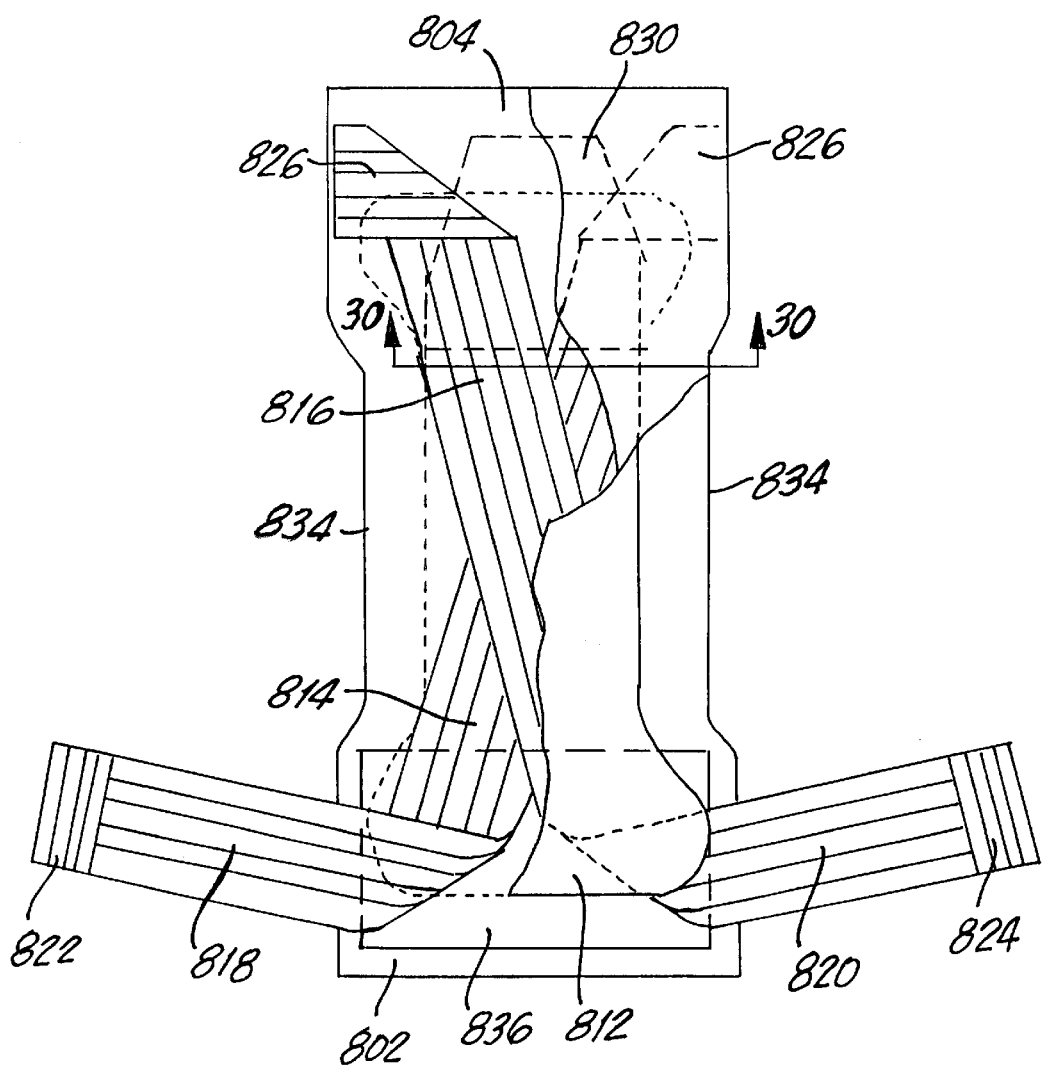
FIG. 28 is a stretched plan view of the embodiment shown in FIG. 27 wherein the front side ends of the bands are folded towards the waist.
Figure 29:
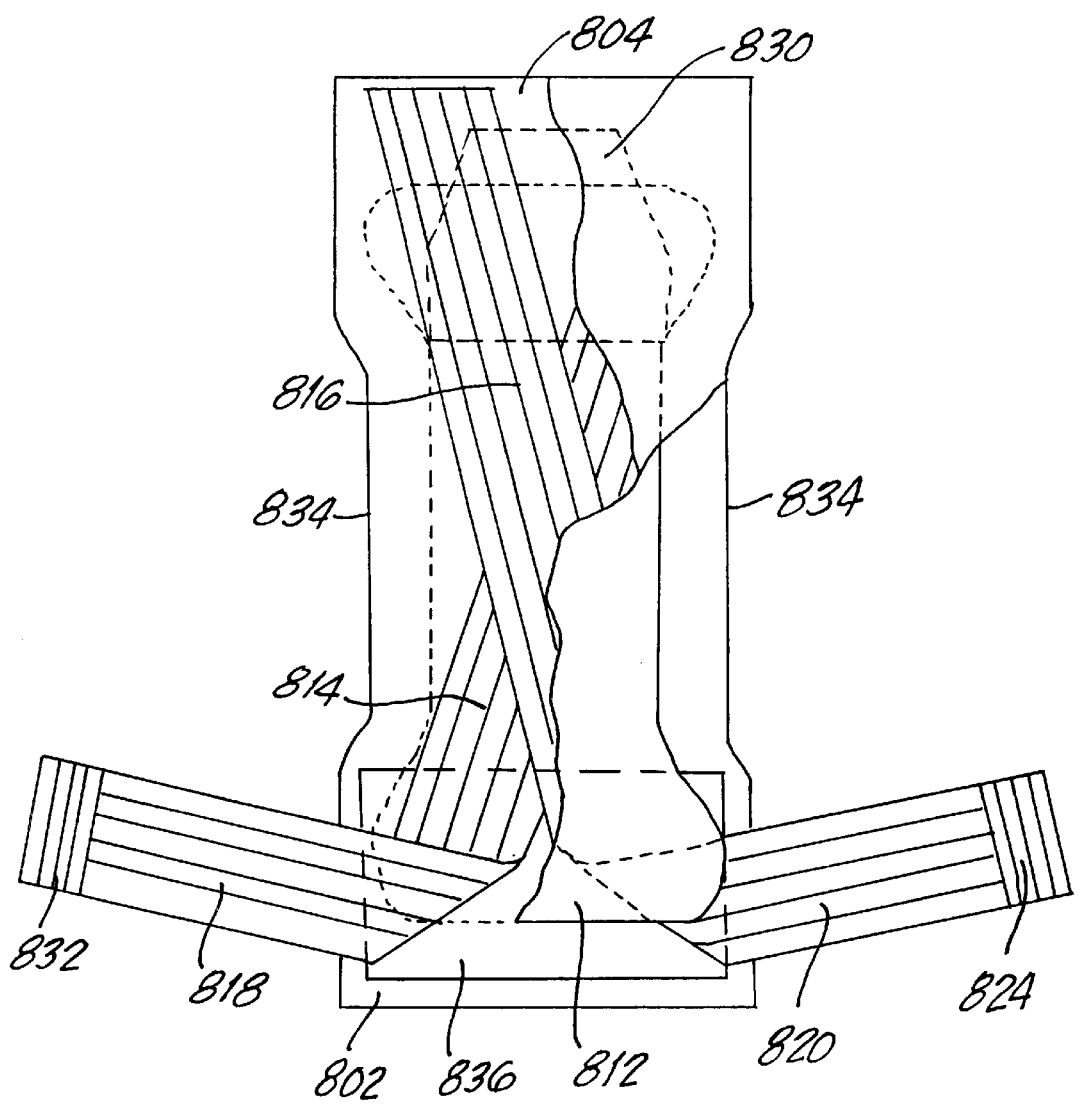
FIG. 29 is a stretched plan view of the embodiment shown in FIG. 27 wherein the front side ends of the bands terminate at the waist.

In the embodiment illustrated in FIGS. 27–30, inclusive, the absorbent article 800 comprises a back waist portion 802, a front waist portion 804, a liquid pervious layer 806, a liquid impervious backsheet 808 and an absorbent pad or layer 810 disposed between the liquid pervious layer and the liquid impervious backsheet. The absorbent article 800 also comprises the contractible tensionable elastic belts 801 on the left and right of the longitudinal axis of the absorbent article (See FIGS. 28 and 29). The belt disposed to the left comprises the longitudinal diagonally disposed inner band portion 814 and the right belt comprises the longitudinal diagonally disposed external and portion 816. The diagonally disposed band portions 814 and 816 cross each other in the crotch region 812 to form a generally V-shaped configuration as shown in FIGS. 28–29. The inner band portion 814 and the outer band portion 816 are folded outwardly in the back waist region 802 into band portions 818 and 820. The left band portion 818 terminates in the closure tab 822 and the right band portion 820 terminates into the end closure tab 824. In the front waist portion 804 the elastic band portions 814 and 816 are folded into the laterally outward portions 826 and 828, respectively, and are attached to the front waist portion (see FIG. 28) or the band portions 814 and 816 may be attached unfolded to the attachment zone 830 as shown in FIG. 29. The elastic belts 801 are attached to the inner side of the liquid impervious backsheet 808 by means of the construction hot melt adhesive 832. The hot melt adhesive is applied intermittently between the liquid impervious layer 810 and the elastic belts 801 when the belts are in stretched condition. Thus, when the belts 801 contract, the absorbent article 801 is rendered elastic in the longitudinal direction between the front and back portions of the absorbent article. Once again, by placing the elastic bands near the leg openings 834, a gasketing seal is formed around each of these openings. The elastic belts 801 are also fastened to the back reinforcement pad 836 by means of the construction adhesive 832.

Figure 30:
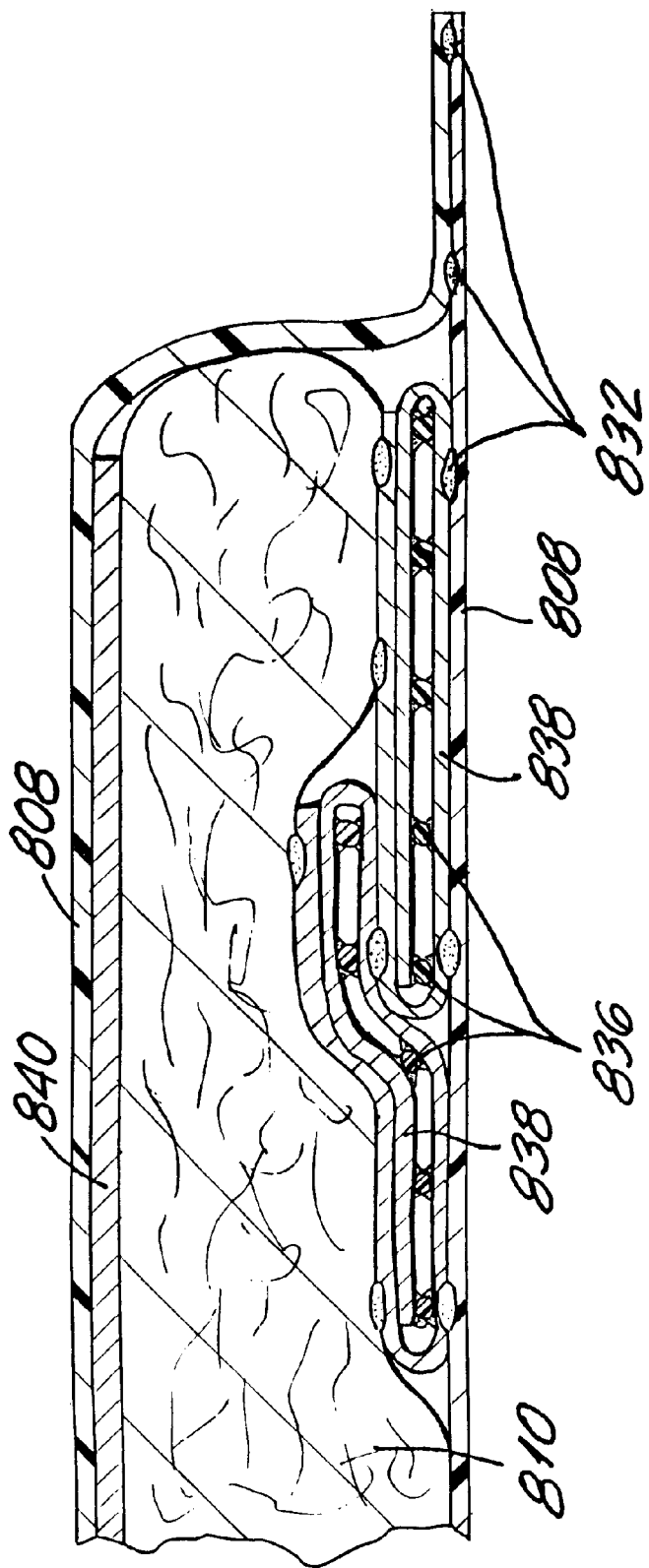
FIG. 30 is a cross sectional view taken along the line 30—30 in FIG. 28 showing the attachment of the bands to the backsheet, and the relative positions of the bands and other components of the article.

As shown in FIG. 30, the elastic belts 801 comprise the elastic elements 838, which are attached to the band wrapping material 838 by means of the adhesive 832. As in the previous embodiments, an acquisition layer 840 is disposed between the liquid pervious layer 806 and the absorbent pad 810.

In use, the absorbent article 800 is placed around the wearer and is adjusted to fit snugly against the wearer's body by stretching the elastic band portions 818 and 820 and securing them by attaching the closure means 822 and 824 to the landing zone 830.

While the present invention has been described and illustrated with reference to several embodiments with certain degree of specificity, other embodiments and modifications are obvious are obvious to those skilled in the art based on the detailed description herein without departing from the scope of the invention. For example, in the embodiment shown in FIGS. 1–5, 6–9, 10–12 and 13–16 the elastic contractible belts are attached to the outside of the absorbent article whereas in the embodiments illustrated in FIGS. 17–19, 20–23, 24–26, and 27–30, the elastic contractible belts are secured to the inside of the absorbent article. Moreover, the elastic contractible belts may be disposed generally parallel to each other and relative to the longitudinal axis of the article as in the embodiments shown in FIGS. 1–5, 6–9, 13–16, 17–19, and 20–23, or these belts may be disposed diagonally, crossing one another in the crotch region as in the embodiments shown in FIGS. 10–12, 14–26 and 27–30. In addition, the elastic belts may be continuous unitary belts, or they may discontinuous, preferably in two segments, as shown in the embodiment in FIG. 2A.

What is claimed is:

1. An integral disposable elasticized absorbent article comprising:
   (a) an absorbent body sharing a longitudinal axis and a horizontal axis, a front waist portion, a back waist portion, a crotch portion and a pair of spaced apart leg openings,
   (b) a liquid pervious top layer facing the body of a wearer of said article,
   (c) a liquid impervious back layer substantially coextensive with said liquid pervious top layer,
   (d) a liquid absorbent layer disposed between said liquid pervious top layer and liquid impervious back layer, said liquid absorbent layer being substantially coextensive with said liquid pervious top layer and said liquid impervious back layer, and
   (e) an attachment zone disposed on said front waist portion, and
   (f) two elasticized band members; a first elasticized band member and a second elasticized band member, said first elasticized band member having a fixed end portion attached to the left side of said absorbent body with said first elasticized band member extending from the front waist to the back waist generally parallel to said longitudinal axis, and wherein said first elasticized band member comprises a portion folded outwardly at an angle relative to said longitudinal axis while being attached to said absorbent body with said outwardly folded portion terminating in a free end portion having an adherent surface adapted to adhere to said attachment zone, said second elasticized band member having a fixed end portion attached to a right side of said absorbent body with said second elasticized band member extending from the front waist to the back waist generally parallel to said longitudinal axis, and wherein said second elasticized band member comprises a portion folded outwardly at an angle relative to said longitudinal axis while being attached to said absorbent body with said outwardly folded portion terminating in a free end portion having an adherent surface adapted to adhere to said attachment zone.

2. An absorbent article as in claim 1 wherein said liquid impervious layer has an inner surface and an outer surface, and one end portion of each of said elasticized band members is attached to the outer surface of said liquid impervious layer.

3. An absorbent article as in claim 2 wherein said elastic band members are prestretched to at least 200 to about 300 percent of the respective initial length of said elastic band member before attachment to said absorbent article.

4. An absorbent article as in claim 3 wherein each of said elasticized band members is disposed diagonally relative to said longitudinal axis.

5. An absorbent article as in claim 2 wherein each of said elasticized band members is disposed diagonally relative to said longitudinal axis.

6. An absorbent article as in claim 1 wherein said liquid impervious layer has an inner surface and an outer surface, and one end portion of each of said elasticized band members is attached to the inner surface of said liquid impervious layer.

7. An absorbent article as in claim 6 wherein said elastic band members are prestretched to at least 200 to about 300 percent of the respective initial length of said elastic band member before attachment to said absorbent article.

8. An absorbent article as in claim 7 wherein each of said elasticized band members is disposed diagonally relative to said longitudinal axis.

9. An absorbent article as in claim 6 wherein each of said elasticized band members is disposed diagonally relative to said longitudinal axis.

10. An absorbent article as in claim 1 wherein said elastic band members are prestretched to at least 200 to about 300 percent of the respective initial length of said elastic band member before attachment to said absorbent article.

11. An absorbent article as in claim 10 wherein each of said elasticized band members is disposed diagonally relative to said longitudinal axis.

12. An absorbent article as in claim 1 wherein each of said elasticized band members is disposed diagonally relative to said longitudinal axis.

* * * * *